(12) United States Patent
Hogue et al.

(10) Patent No.: US 7,741,270 B2
(45) Date of Patent: Jun. 22, 2010

(54) LUMINESCENT MARKERS

(75) Inventors: Christopher Hogue, 2373 Eden Valley Dr., Oakville, Ontario (CA) M5G 1X5; Susanna Sroka, 1021 Knotty Pine Grove, Mississauga, Ontario (CA) L5W 1J7

(73) Assignees: Christopher Hogue, Toronto, Ontario (CA); Susanna Sroka, Surrey, British Colombia (CA)

( * ) Notice: Subject to any disclaimer, the term of this patent is extended or adjusted under 35 U.S.C. 154(b) by 1081 days.

(21) Appl. No.: 10/961,645

(22) Filed: Oct. 8, 2004

(65) Prior Publication Data

US 2005/0158794 A1    Jul. 21, 2005

Related U.S. Application Data

(63) Continuation of application No. PCT/CA03/00546, filed on Apr. 11, 2003.

(60) Provisional application No. 60/372,382, filed on Apr. 11, 2002.

(51) Int. Cl.
*A01N 37/18* (2006.01)
*C07K 14/00* (2006.01)
*C12P 21/00* (2006.01)

(52) U.S. Cl. .......................................... 514/2; 530/350
(58) Field of Classification Search ...................... None
See application file for complete search history.

(56) References Cited

FOREIGN PATENT DOCUMENTS

WO    WO98/40477    *    9/1998

OTHER PUBLICATIONS

Chalfie et al. Green Fluorescent Protein as a Marker for Gene Expression. Science 263: 802-805, 1994.*
Zheng et al. Effects of metal binding affinity on the chemical and thermal stability of site-directed mutants of rat oncomodulin. Biophysical Chem. 71: 157-172, 1998.*

* cited by examiner

*Primary Examiner*—Christopher S. F. Low
*Assistant Examiner*—Michele K Joike
(74) *Attorney, Agent, or Firm*—Merchant & Gould P.C.

(57) ABSTRACT

The invention relates to luminescent proteins, nucleic acids encoding same, compositions and combinations comprising the proteins, and methods using the proteins, nucleic acids, compositions and combinations. In particular, a luminescent protein is provided comprising oncomodulin in which a salt bridge has been introduced to provide greater stability. The protein may be used as a luminescent marker in, for example, luminescent items, immunoassays, and fluorescent energy transfer assays.

29 Claims, 16 Drawing Sheets

Figure 1A

```
  1-ATGAGCATTACCGATATTTTATCTGCCGAAGACATCGCGGCAGCCCTTCAGGAATGCCAA-60
 61-GATCCAGACACCTTCGAGCCAAAAAAGTTTTTCCAAACCAGCGGACTGAAAAAGAAATCT-120
121-GCCAGTCAAGTAAAAGATATTTGGCGTTTTATTGATAAAAACGCGGACGGATGGATTGAA-180
181-TTTGAAGAACTGAAATATTTCTTGCAAAAATTCCAAAGTGATGCTCGTGAGCTGACCGAA-240
241-TCCGAAACCAAGTCTTTGATGGACGCAGCGGATAACGACGGTGATGGTAAGATTGGAGCT-300
301-GATGAGTTCCAAGAAATGGTAGCTGAATCCTAA-333
```

Figure 1B

```
  1-ATGGTGAGCAAGGGCGAGGAGCTGTTCACCGGGGTGGTGCCCATCCTGGTCGAGCTGGAC-60
 61-GGCGACGTAAACGGCCACAAGTTCAGCGTGTCCGGCGAGGGCGAGGGCGATGCCACCTAC-120
121-GGCAAGCTGACCCTGAAGTTCATCTGCACCACCGGCAAGCTGCCCGTGCCCTGGCCCACC-180
181-CTCGTGACCACCCTGACCTACGGCGTGCAGTGCTTCAGCCGCTACCCCGACCACATGAAG-240
241-CAGCACGACTTCTTCAAGTCCGCCATGCCCGAAGGCTACGTCCAGGAGCGCACCATCTTC-300
301-TTCAAGGACGACGGCAACTACAAGACCCGCGCCGAGGTGAAGTTCGAGGGCGACACCCTG-360
361-GTGAACCGCATCGAGCTGAAGGGCATCGACTTCAAGGAGGACGGCAACATCCTGGGGCAC-420
421-AAGCTGGAGTACAACTACAACAGCCACAACGTCTATATCATGGCCGACAAGCAGAAGAAC-480
481-GGCATCAAGGTGAACTTCAAGATCCGCCACAACATCGAGGACGGCAGCGTGCAGCTCGCC-540
541-GACCACTACCAGCAGAACACCCCCATCGGCGACGGCCCCGTGCTGCTGCCCGACAACCAC-600
601-TACCTGAGCACCCAGTCCGCCCTGAGCAAAGACCCCAACGAGAAGCGCGATCACATGGTC-660
661-CTGCTGGAGTTCGTGACCGCCGCCGGGATCACTCTCGGCATGGACGAGCTGTACAAGTAA-720
```

Figure 1C

```
   1-ATGAGCATTACCGATATTTTATCTGCCGAAGACATCGCGGCAGCCCTTCAGGAATGCCAA-60
  61-GATCCAGACACCTTCGAGCCAAAAAAGTTTTTCCAAACCAGCGGACTGAAAAAGAAATCT-120
 121-GCCAGTCAAGTAAAAGATATTTGGCGTTTTATTGATAAAAACGCGGACGGATGGATTGAA-180
 181-TTTGAAGAACTGAAATATTTCTTGCAAAAATTCCAAAGTGATGCTCGTGAGCTGACCGAA-240
 241-TCCGAAACCAAGTCTTTGATGGACGCAGCGGATAACGACGGTGATGGTAAGATTGGAGCT-300
 301-GATGAGTTCCAAGAAATGGTAGCTGAATCCACCATGGTGAGCAAGGGCGAGGAGCTGTTC-360
 361-ACCGGGGTGGTGCCCATCCTGGTCGAGCTGGACGGCGACGTAAACGGCCACAAGTTCAGC-420
 421-GTGTCCGGCGAGGGCGAGGGCGATGCCACCTACGGCAAGCTGACCCTGAAGTTCATCTGC-480
 481-ACCACCGGCAAGCTGCCCGTGCCCTGGCCCACCCTCGTGACCACCCTGACCTACGGCGTG-540
 541-CAGTGCTTCAGCCGCTACCCCGACCACATGAAGCAGCACGACTTCTTCAAGTCCGCCATG-600
 601-CCCGAAGGCTACGTCCAGGAGCGCACCATCTTCTTCAAGGACGACGGCAACTACAAGACC-660
 661-CGCGCCGAGGTGAAGTTCGAGGGCGACACCCTGGTGAACCGCATCGAGCTGAAGGGCATC-720
 721-GACTTCAAGGAGGACGGCAACATCCTGGGGCACAAGCTGGAGTACAACTACAACAGCCAC-780
 781-AACGTCTATATCATGGCCGACAAGCAGAAGAACGGCATCAAGGTGAACTTCAAGATCCGC-840
 841-CACAACATCGAGGACGGCAGCGTGCAGCTCGCCGACCACTACCAGCAGAACACCCCCATC-900
 901-GGCGACGGCCCCGTGCTGCTGCCCGACAACCACTACCTGAGCACCCAGTCCGCCCTGAGC-960
 961-AAAGACCCCAACGAGAAGCGCGATCACATGGTCCTGCTGGAGTTCGTGACCGCCGCCGGG-1020
1021-ATCACTCTCGGCATGGACGAGCTGTACAAGTAA-1053
```

Figure 2

```
OM      SITDILSAED IAAALQECQD PDTFEPQKFF QTSGLSKMSA SQVKDIFRFI
TBF     SITDILSAED IAAALQECQD PDTFEPKKFF QTSGLKKKSA SQVKDIWRFI
                   60         70         80         90
        100
OM      DNDQSGYLDG DELKYFLQKF QSDARELTES ETKSLMDAAD NDGDGKIGAD
TBF     DKNADGWIEF EELKYFLQKF QSDARELTES ETKSLMDAAD NDGDGKIGAD

OM      EFQEMVHS
TBF     EFQEMVAES
```

Figure 3

|  | 10 | 20 | 30 | 40 | 50 |
|---|---|---|---|---|---|
| TBFEGFP | SITDILSAED | IAAALQECQD | PDTFEPKKFF | QTSGLKKKSA | SQVKDIWRFI |
| EGFP | | | | | |

|  | 60 | 70 | 80 | 90 | 100 |
|---|---|---|---|---|---|
| TBFEGFP | DKNADGWIEF | EELKYFLQKF | QSDARELTES | ETKSLMDAAD | NDGDGKIGAD |
| EGFP | | | | | |

|  | 110 | 120 | 130 | 140 | 150 |
|---|---|---|---|---|---|
| TBFEGFP | EFQEMVAEST | MVSKGEELFT | GVVPILVELD | GDVNGHKFSV | SGEGEGDATY |
| EGFP | | VSKGEELFT | GVVPILVELD | GDVNGHKFSV | SGEGEGDATY |

|  | 160 | 170 | 180 | 190 | 200 |
|---|---|---|---|---|---|
| TBFEGFP | GKLTLKFICT | TGKLPVPWPT | LVTTLTYGVQ | CFSRYPDHMK | QHDFFKSAMP |
| EGFP | GKLTLKFICT | TGKLPVPWPT | LVTTLTYGVQ | CFSRYPDHMK | QHDFFKSAMP |

|  | 210 | 220 | 230 | 240 | 250 |
|---|---|---|---|---|---|
| TBFEGFP | EGYVQERTIF | FKDDGNYKTR | AEVKFEGDTL | VNRIELKGID | FKEDGNILGH |
| EGFP | EGYVQERTIF | FKDDGNYKTR | AEVKFEGDTL | VNRIELKGID | FKEDGNILGH |

|  | 260 | 270 | 280 | 290 | 300 |
|---|---|---|---|---|---|
| TBFEGFP | KLEYNYNSHN | VYIMADKQKN | GIKVNFKIRH | NIEDGSVQLA | DHYQQNTPIG |
| EGFP | KLEYNYNSHN | VYIMADKQKN | GIKVNFKIRH | NIEDGSVQLA | DHYQQNTPIG |

|  | 310 | 320 | 330 | 340 | 350 |
|---|---|---|---|---|---|
| TBFEGFP | DGPVLLPDNH | YLSTQSALSK | DPNEKRDHMV | LLEFVTAAGI | TLGMDELYK |
| EGFP | DGPVLLPDNH | YLSTQSALSK | DPNEKRDHMV | LLEFVTAAGI | TLGMDELYK |

Figure 6
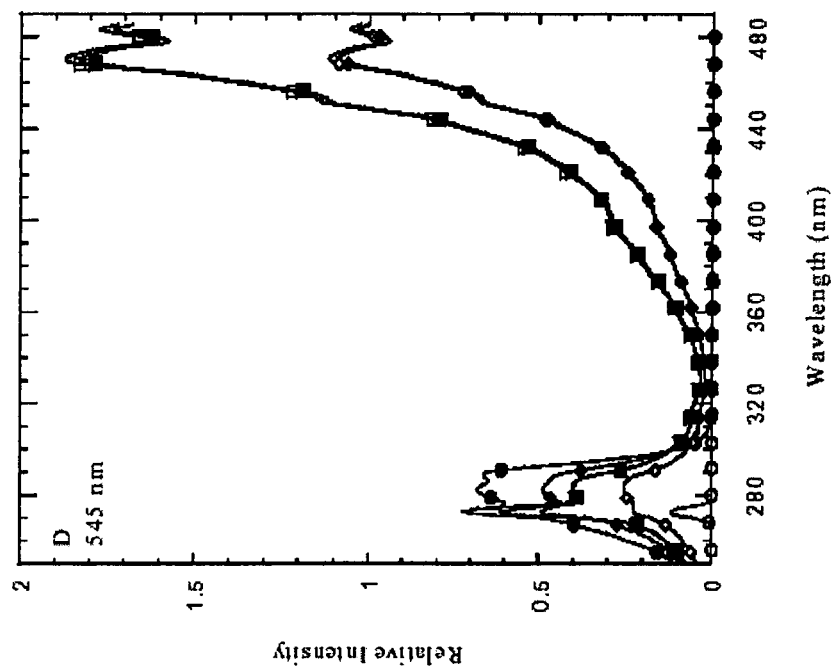
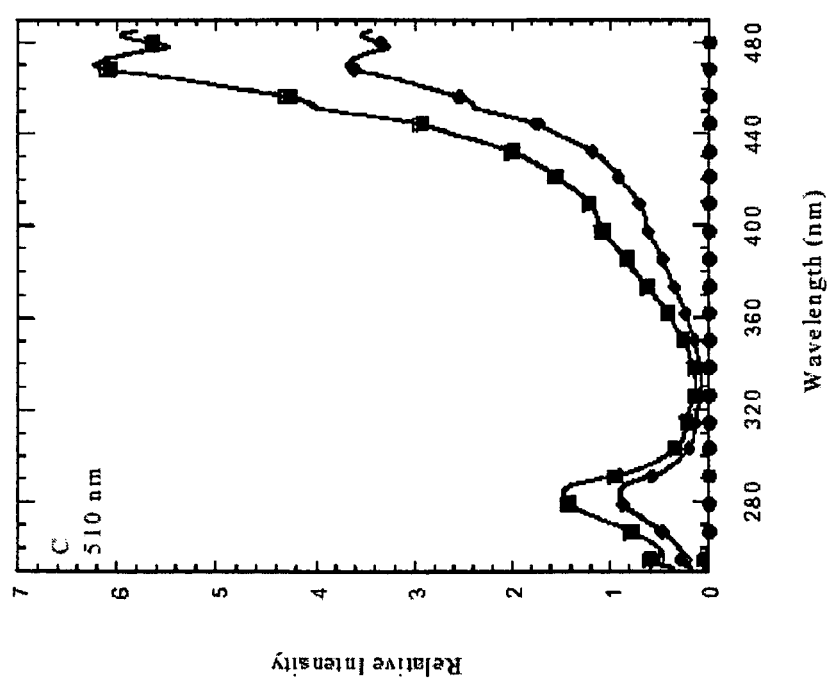

Figure 7
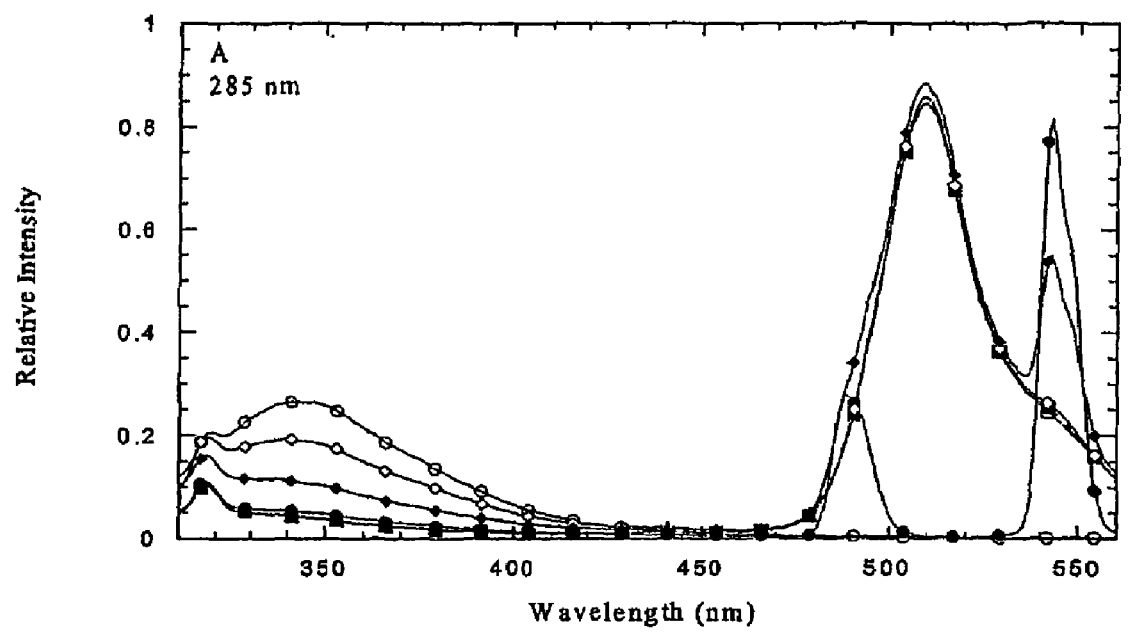
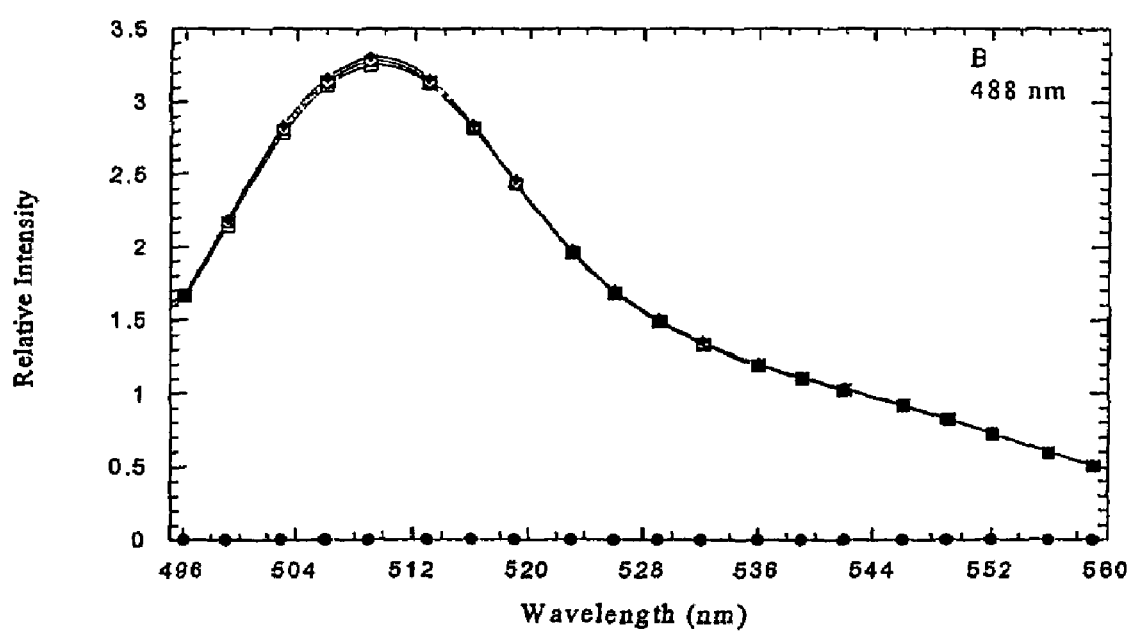

Figure 11

|      | 10 | 20 | 30 | 40 |
|------|----|----|----|----|
| 50   |    |    |    |    |
| TTE  | SITDILSAED | IAAALQECQD | PDTFEPKKFF | QTSGLKKKSA SQVKDIWRFI |

|      | 60 | 70 | 80 | 90 |
|------|----|----|----|----|
| 100  |    |    |    |    |
| TTE  | DKNADGWIEF | EELKYFLQKF | QSDARELTES | ETKSLMDAAD NDGDGKIGAD |

|      | 110 | 120 | 130 | 140 |
|------|-----|-----|-----|-----|
| 150  |     |     |     |     |
| TTE  | EFQEMVAESG | GGGENLYFQG | GGGGTMVSKG | EELFTGVVPI LVELDGDVNG |

|      | 160 | 170 | 180 | 190 |
|------|-----|-----|-----|-----|
| 200  |     |     |     |     |
| TTE  | HKFSVSGEGE | GDATYGKLTL | KFICTTGKLP | VPWPTLVTTL TYGVQCFSRY |

|      | 210 | 220 | 230 | 240 |
|------|-----|-----|-----|-----|
| 250  |     |     |     |     |
| TTE  | PDHMKQHDFF | KSAMPEGYVQ | ERTIFFKDDG | NYKTRAEVKF EGDTLVNRIE |

|      | 260 | 270 | 280 | 290 |
|------|-----|-----|-----|-----|
| 300  |     |     |     |     |
| TTE  | LKGIDFKEDG | NILGHKLEYN | YNSHNVYIMA | DKQKNGIKVN FKIRHNIEDG |

|      | 310 | 320 | 330 | 340 |
|------|-----|-----|-----|-----|
| 350  |     |     |     |     |
| TTE  | SVQLADHYQQ | NTPIGDGPVL | LPDNHYLSTQ | SALSKDPNEK RDHMVLLEFV |

|      | 360 | | | |
|------|-----|---|---|---|
| TTE  | TAAGITLGMD ELYK | | | |

Figure 13
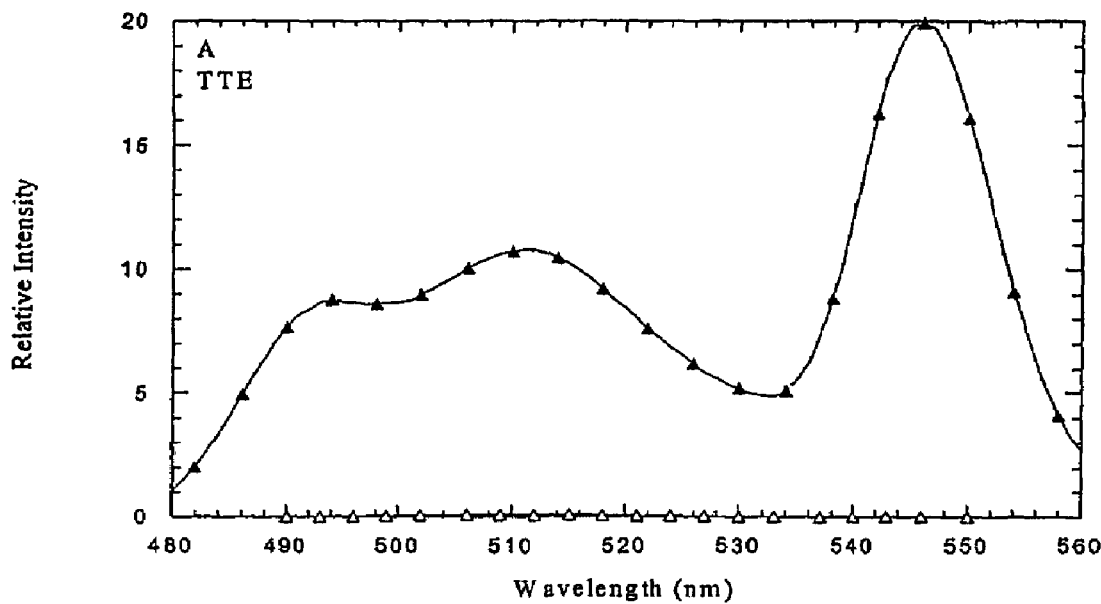
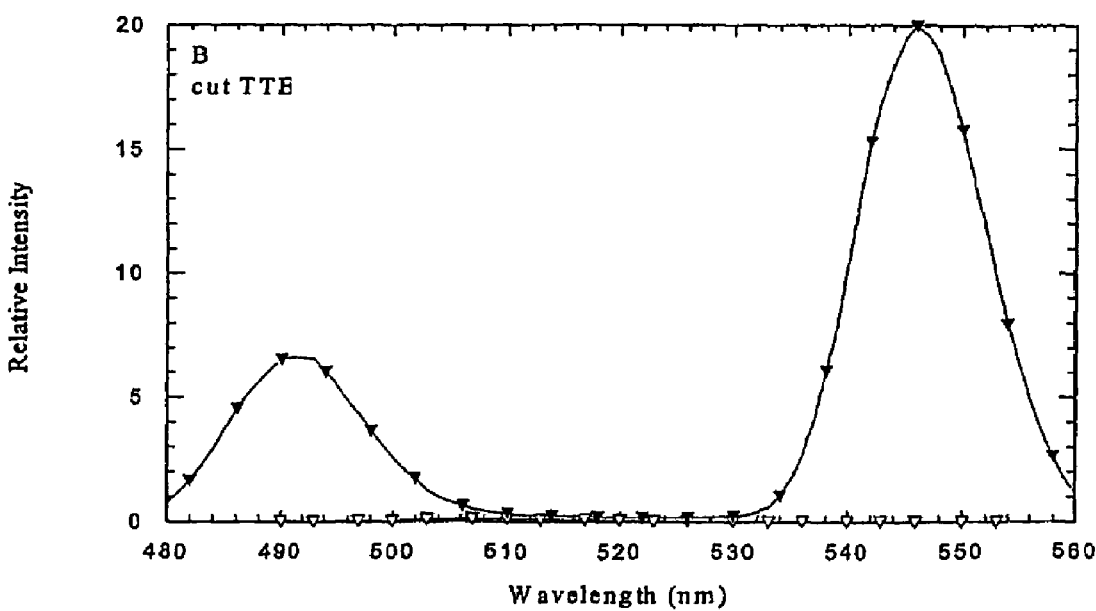

SEQUENCE LISTING

<160> NUMBER OF SEQ ID NOS: 16

<210> SEQ ID NO 1
<211> LENGTH: 333
<212> TYPE: DNA
<213> ORGANISM: Artificial
<220> FEATURE:
<223> OTHER INFORMATION: nucleic acid sequence encoding a TBF protein

<400> SEQUENCE: 1

```
atgagcatta ccgatatttt atctgccgaa gacatcgcgg cagcccttca ggaatgccaa      60
gatccagaca ccttcgagcc aaaaaagttt ttccaaacca gcggactgaa aagaaatct     120 gccagtcaag taaagatat ttggcgtttt attgataaaa acgcggacgg atggattgaa     180
tttgaagaac tgaaatattt cttgcaaaaa ttccaaagtg atgctcgtga gctgaccgaa     240
tccgaaacca gtctttgat ggacgcagcg ataacgacg gtgatggtaa gattggagct      300
gatgagttcc aagaaatggt agctgaatcc taa                                 333
```

<210> SEQ ID NO 2
<211> LENGTH: 720
<212> TYPE: DNA
<213> ORGANISM: Artificial
<220> FEATURE:
<223> OTHER INFORMATION: nucleic acid sequence encoding EGFP (Enhanced
      Green Fluorescent Protein)

<400> SEQUENCE: 2

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 3
<211> LENGTH: 1053
<212> TYPE: DNA
<213> ORGANISM: Artificial
<220> FEATURE:
<223> OTHER INFORMATION: nucleic acid sequence encoding a chimeric
      protein comprising TBF and EGFP

<400> SEQUENCE: 3

```
atgagcatta ccgatatttt atctgccgaa gacatcgcgg cagcccttca ggaatgccaa      60
gatccagaca ccttcgagcc aaaaaagttt ttccaaacca gcggactgaa aagaaatct     120 gccagtcaag taaagatat ttggcgtttt attgataaaa acgcggacgg atggattgaa     180
tttgaagaac tgaaatattt cttgcaaaaa ttccaaagtg atgctcgtga gctgaccgaa     240
```

```
tccgaaaccaagtctttgatggacgcagcggataacgacggtgatggtaagattggagct    300 gatgagttccaagaaatggtagctgaatccaccatggtgagcaagggcgaggagctgttc    360 accggggtggtgcccatcctggtcgagctgacggcgacgtaaacggccacaagttcagc    420 gtgtccggcgagggcgagggcgatgccacctacggcaagctgaccctgaagttcatctgc    480 accaccggcaagctgcccgtgccctggcccaccctcgtgaccaccctgacctacggcgtg    540 cagtgcttcagccgctacccccgaccacatgaagcagcacgacttcttcaagtccgccatg    600 cccgaaggctacgtccaggagcgcaccatcttcttcaaggacgacggcaactacaagacc    660 cgcgccgagtgaagttcgagggcgacaccctggtgaaccgcatcgagctgaagggcatc    720 gacttcaaggaggacggcaacatcctggggcacaagctggagtacaactacaacagccac    780 aacgtctatatcatggccgacaagcagaagaacggcatcaaggtgaacttcaagatccgc    840 cacaacatcgaggacggcagcgtgcagctcgccgaccactaccagcagaacacccccatc    900 ggcgacggccccgtgctgctgcccgacaaccactacctgagcacccagtccgccctgagc    960 aaagaccccaacgagaagcgcgatcacatggtcctgctggagttcgtgaccgccgccggg    1020 atcactctcggcatggacgagctgtacaagtaa    1053
```

<210> SEQ ID NO 4
<211> LENGTH: 108
<212> TYPE: PRT
<213> ORGANISM: Rat

<400> SEQUENCE: 4

```
Ser Ile Thr Asp Ile Leu Ser Ala Glu Asp Ile Ala Ala Ala Leu Gln
1               5                   10                  15

Glu Cys Gln Asp Pro Asp Thr Phe Glu Pro Gln Lys Phe Phe Gln Thr
            20                  25                  30

Ser Gly Leu Ser Lys Met Ser Ala Ser Gln Val Lys Asp Ile Phe Arg
        35                  40                  45

Phe Ile Asp Asn Asp Gln Ser Gly Tyr Leu Asp Gly Asp Glu Leu Lys
    50                  55                  60

Tyr Phe Leu Gln Lys Phe Gln Ser Asp Ala Arg Glu Leu Thr Glu Ser
65                  70                  75                  80

Glu Thr Lys Ser Leu Met Asp Ala Ala Asp Asn Asp Gly Asp Gly Lys
                85                  90                  95

Ile Gly Ala Asp Glu Phe Gln Glu Met Val His Ser
            100                 105
```

<210> SEQ ID NO 5
<211> LENGTH: 109
<212> TYPE: PRT
<213> ORGANISM: Artificial
<220> FEATURE:
<223> OTHER INFORMATION: amino acid sequence for a TBF protein

<400> SEQUENCE: 5

```
Ser Ile Thr Asp Ile Leu Ser Ala Glu Asp Ile Ala Ala Ala Leu Gln
1               5                   10                  15

Glu Cys Gln Asp Pro Asp Thr Phe Glu Pro Lys Lys Phe Phe Gln Thr
            20                  25                  30

Ser Gly Leu Lys Lys Lys Ser Ala Ser Gln Val Lys Asp Ile Trp Arg
        35                  40                  45

Phe Ile Asp Lys Asn Ala Asp Gly Trp Ile Glu Phe Glu Glu Leu Lys
    50                  55                  60
```

```
Tyr Phe Leu Gln Lys Phe Gln Ser Asp Ala Arg Glu Leu Thr Glu Ser
65                  70                  75                  80

Glu Thr Lys Ser Leu Met Asp Ala Ala Asp Asn Asp Gly Asp Gly Lys
                85                  90                  95

Ile Gly Ala Asp Glu Phe Gln Glu Met Val Ala Glu Ser
            100                 105
```

<210> SEQ ID NO 6
<211> LENGTH: 349
<212> TYPE: PRT
<213> ORGANISM: Artificial
<220> FEATURE:
<223> OTHER INFORMATION: amino acid sequence for a chimeric protein comprising TBF and EGFP

<400> SEQUENCE: 6

```
Ser Ile Thr Asp Ile Leu Ser Ala Glu Asp Ile Ala Ala Ala Leu Gln
1               5                   10                  15

Glu Cys Gln Asp Pro Asp Thr Phe Glu Pro Lys Lys Phe Phe Gln Thr
                20                  25                  30

Ser Gly Leu Lys Lys Lys Ser Ala Ser Gln Val Lys Asp Ile Trp Arg
            35                  40                  45

Phe Ile Asp Lys Asn Ala Asp Gly Trp Ile Glu Phe Glu Glu Leu Lys
50                  55                  60

Tyr Phe Leu Gln Lys Phe Gln Ser Asp Ala Arg Glu Leu Thr Glu Ser
65                  70                  75                  80

Glu Thr Lys Ser Leu Met Asp Ala Ala Asp Asn Asp Gly Asp Gly Lys
                85                  90                  95

Ile Gly Ala Asp Glu Phe Gln Glu Met Val Ala Glu Ser Thr Met Val
            100                 105                 110

Ser Lys Gly Glu Glu Leu Phe Thr Gly Val Val Pro Ile Leu Val Glu
            115                 120                 125

Leu Asp Gly Asp Val Asn Gly His Lys Phe Ser Val Ser Gly Glu Gly
130                 135                 140

Glu Gly Asp Ala Thr Tyr Gly Lys Leu Thr Leu Lys Phe Ile Cys Thr
145                 150                 155                 160

Thr Gly Lys Leu Pro Val Pro Trp Pro Thr Leu Val Thr Thr Leu Thr
                165                 170                 175

Tyr Gly Val Gln Cys Phe Ser Arg Tyr Pro Asp His Met Lys Gln His
            180                 185                 190

Asp Phe Phe Lys Ser Ala Met Pro Glu Gly Tyr Val Gln Glu Arg Thr
        195                 200                 205

Ile Phe Phe Lys Asp Asp Gly Asn Tyr Lys Thr Arg Ala Glu Val Lys
210                 215                 220

Phe Glu Gly Asp Thr Leu Val Asn Arg Ile Glu Leu Lys Gly Ile Asp
225                 230                 235                 240

Phe Lys Glu Asp Gly Asn Ile Leu Gly His Lys Leu Glu Tyr Asn Tyr
                245                 250                 255

Asn Ser His Asn Val Tyr Ile Met Ala Asp Lys Gln Lys Asn Gly Ile
            260                 265                 270

Lys Val Asn Phe Lys Ile Arg His Asn Ile Glu Asp Gly Ser Val Gln
        275                 280                 285

Leu Ala Asp His Tyr Gln Gln Asn Thr Pro Ile Gly Asp Gly Pro Val
290                 295                 300

Leu Leu Pro Asp Asn His Tyr Leu Ser Thr Gln Ser Ala Leu Ser Lys
```

```
                305                 310                 315                 320
Asp Pro Asn Glu Lys Arg Asp His Met Val Leu Leu Glu Phe Val Thr
                    325                 330                 335

Ala Ala Gly Ile Thr Leu Gly Met Asp Glu Leu Tyr Lys
                340                 345

<210> SEQ ID NO 7
<211> LENGTH: 238
<212> TYPE: PRT
<213> ORGANISM: Artificial
<220> FEATURE:
<223> OTHER INFORMATION: amino acid sequence for EGFP

<400> SEQUENCE: 7

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 8
<211> LENGTH: 364
<212> TYPE: PRT
<213> ORGANISM: Artificial
<220> FEATURE:
<223> OTHER INFORMATION: amino acid sequence for TTE - chimeric protein
      TBF-EGFP engineered to contain the TEV protease recognition
      sequence

<400> SEQUENCE: 8

Ser Ile Thr Asp Ile Leu Ser Ala Glu Asp Ile Ala Ala Ala Leu Gln
1               5                   10                  15

Glu Cys Gln Asp Pro Asp Thr Phe Glu Pro Lys Lys Phe Phe Gln Thr
```

```
                    20                  25                  30
Ser Gly Leu Lys Lys Ser Ala Ser Gln Val Lys Asp Ile Trp Arg
        35                  40                  45

Phe Ile Asp Lys Asn Ala Asp Gly Trp Ile Glu Phe Glu Glu Leu Lys
50                  55                  60

Tyr Phe Leu Gln Lys Phe Gln Ser Asp Ala Arg Glu Leu Thr Glu Ser
65                  70                  75                  80

Glu Thr Lys Ser Leu Met Asp Ala Ala Asp Asn Asp Gly Asp Gly Lys
                85                  90                  95

Ile Gly Ala Asp Glu Phe Gln Glu Met Val Ala Glu Ser Gly Gly Gly
            100                 105                 110

Gly Glu Asn Leu Tyr Phe Gln Gly Gly Gly Gly Thr Met Val Ser
        115                 120                 125

Lys Gly Glu Glu Leu Phe Thr Gly Val Val Pro Ile Leu Val Glu Leu
130                 135                 140

Asp Gly Asp Val Asn Gly His Lys Phe Ser Val Ser Gly Glu Gly Glu
145                 150                 155                 160

Gly Asp Ala Thr Tyr Gly Lys Leu Thr Leu Lys Phe Ile Cys Thr Thr
                165                 170                 175

Gly Lys Leu Pro Val Pro Trp Pro Thr Leu Val Thr Thr Leu Thr Tyr
            180                 185                 190

Gly Val Gln Cys Phe Ser Arg Tyr Pro Asp His Met Lys Gln His Asp
        195                 200                 205

Phe Phe Lys Ser Ala Met Pro Glu Gly Tyr Val Gln Glu Arg Thr Ile
210                 215                 220

Phe Phe Lys Asp Asp Gly Asn Tyr Lys Thr Arg Ala Glu Val Lys Phe
225                 230                 235                 240

Glu Gly Asp Thr Leu Val Asn Arg Ile Glu Leu Lys Gly Ile Asp Phe
                245                 250                 255

Lys Glu Asp Gly Asn Ile Leu Gly His Lys Leu Glu Tyr Asn Tyr Asn
            260                 265                 270

Ser His Asn Val Tyr Ile Met Ala Asp Lys Gln Lys Asn Gly Ile Lys
        275                 280                 285

Val Asn Phe Lys Ile Arg His Asn Ile Glu Asp Gly Ser Val Gln Leu
290                 295                 300

Ala Asp His Tyr Gln Gln Asn Thr Pro Ile Gly Asp Gly Pro Val Leu
305                 310                 315                 320

Leu Pro Asp Asn His Tyr Leu Ser Thr Gln Ser Ala Leu Ser Lys Asp
                325                 330                 335

Pro Asn Glu Lys Arg Asp His Met Val Leu Leu Glu Phe Val Thr Ala
            340                 345                 350

Ala Gly Ile Thr Leu Gly Met Asp Glu Leu Tyr Lys
        355                 360

<210> SEQ ID NO 9
<211> LENGTH: 33
<212> TYPE: DNA
<213> ORGANISM: Artificial
<220> FEATURE:
<223> OTHER INFORMATION: primer

<400> SEQUENCE: 9
cgcgccatgg tggattcagc taccatttct tgg                               33

<210> SEQ ID NO 10
```

```
<211> LENGTH: 27
<212> TYPE: DNA
<213> ORGANISM: Artificial
<220> FEATURE:
<223> OTHER INFORMATION: primer

<400> SEQUENCE: 10
gcgcctgcag gatgagcatt accgata                                       27

<210> SEQ ID NO 11
<211> LENGTH: 101
<212> TYPE: DNA
<213> ORGANISM: Artificial
<220> FEATURE:
<223> OTHER INFORMATION: primer

<400> SEQUENCE: 11
cgcgccatgg taccgccacc gccaccctga aaatacaaat tctcgccacc gccaccggat   60
tcagctacca tttcttggaa ctcatcagct ccaatcttac c                      101

<210> SEQ ID NO 12
<211> LENGTH: 12
<212> TYPE: PRT
<213> ORGANISM: Rat

<400> SEQUENCE: 12

Asp Asn Asp Gln Ser Gly Tyr Leu Asp Gly Asp Glu
1               5                   10

<210> SEQ ID NO 13
<211> LENGTH: 12
<212> TYPE: PRT
<213> ORGANISM: Artificial
<220> FEATURE:
<223> OTHER INFORMATION: aritifical replacement sequence for the CD loop
      of oncomodulin

<400> SEQUENCE: 13

Asp Lys Asn Ala Asp Gly Trp Ile Glu Phe Glu Glu
1               5                   10

<210> SEQ ID NO 14
<211> LENGTH: 7
<212> TYPE: PRT
<213> ORGANISM: Artificial
<220> FEATURE:
<223> OTHER INFORMATION: TEV protease recognition sequence

<400> SEQUENCE: 14

Glu Asn Leu Tyr Phe Gln Gly
1               5

<210> SEQ ID NO 15
<211> LENGTH: 21
<212> TYPE: DNA
<213> ORGANISM: Artificial
<220> FEATURE:
<223> OTHER INFORMATION: polynucleotide encoding a TEV recognition
      sequence

<400> SEQUENCE: 15
accctgaaaa tacaaattct c                                             21

<210> SEQ ID NO 16
<211> LENGTH: 12
<212> TYPE: PRT
```

-continued

```
<213> ORGANISM: Artificial
<220> FEATURE:
<223> OTHER INFORMATION: artificial sequence replacing the CD loop of
      oncomodulin

<400> SEQUENCE: 16

Asp Met Asn Ala Gly Asp Trp Ile Glu Phe Glu Glu
1               5                   10
```

US 7,741,270 B2

LUMINESCENT MARKERS

FIELD OF THE INVENTION

The invention relates to luminescent proteins, nucleic acids encoding same, compositions, complexes, and combinations comprising the proteins, and methods using the proteins, nucleic acids, complexes, compositions and combinations.

BACKGROUND OF THE INVENTION

Luminescent (including fluorescent and phosphorescent) markers have a wide variety of applications in science, medicine and engineering. In many cases, these markers provide competitive replacements for radiolabels, chromogens, radiation-dense dyes, etc. However, a significant limitation to the use of luminescent markers is generating an acceptable signal-to-noise ratio. Marker-dependent properties such as absorption and emission maxima, Stoke's shift, quantum yield, etc. affect the ability to distinguish signal from auto- or background fluorescence. Therefore, there is a continuous need to provide improved luminescent markers; especially luminescent markers with long-lived luminescence, and/or a large Stoke's shift with long wavelength emissions. Other useful and desirable properties include: easy and cost-effective synthesis; chemical and thermal stability; convenient attachment to a wide variety of macromolecules including proteins and nucleic acids; efficient excitability; capable of intense luminescence; and the capacity to perform as good luminescent resonance-energy transfer donors.

SUMMARY OF THE INVENTION

Applicants have produced an oncomodulin mutant that has unexpected advantages including but not limited to enhanced luminescence and thermostability.

Therefore, the invention provides a protein comprising oncomodulin in which one or more salt bridge and/or hydrogen bonding network has been introduced to provide greater stability when compared to a native oncomodulin or CDOM33.

In another aspect the invention provides an oncomodulin mutant protein comprising oncomodulin in which a CD-loop of oncomodulin is replaced with a more potent metal binding site and Phe47 is replaced with Trp47.

A protein of the invention may also be characterized by one or more of the following: (a) Gln27 of oncomodulin is replaced with Lys27, (b) Ser36 of oncomodulin is replaced with Lys36, (c) extended C, terminus, and (d) enhanced $Tb^{3+}$ luminescence (e.g. luminescence is enhanced by at least 10%, 15%, 17%, 20%, or 25% relative to CDOM33). A TBF protein may also be characterized as having long-lived luminescence and a large Stoke's shift with long wavelength emission.

In an embodiment, the CD loop of oncomodulin is replaced with DKNADGWIEFEE (SEQ ID NO. 13).

In a particular embodiment, the invention contemplates an oncomodulin mutant protein comprising an amino acid sequence of SEQ ID NO. 5.

The invention also contemplates a truncation, an analog, variant, or a protein having substantial sequence identity to an oncomodulin mutant protein of the invention. An oncomodulin mutant protein of the invention including truncations, analogs, variants, and proteins with substantial sequence identity are referred to herein as "TBF", "TBF protein", or "luminescent protein".

In an aspect the invention provides a fusion or chimeric protein (also referred to herein as "chimeric TBF protein") comprising a TBF protein of the invention associated or conjugated with one or more molecule. The molecule may be a luminescent agent acceptor or target peptide (e.g. an enzyme recognition site). A chimeric protein may comprise a TBF protein and a luminescent agent acceptor linked via a target peptide. In a particular embodiment, a chimeric protein of the invention comprises (a) a TBF protein and a green fluorescent protein (GFP), (b) a TBF protein and an enzyme recognition site, or (c) a TBF protein, GFP, and an enzyme recognition site. In a particular embodiment the GFP is EGFP encoded by the sequence of SEQ ID NO.2 or comprising the sequence of SEQ ID NO 7.

The invention contemplates an antibody that specifically binds to a protein of the invention.

In another aspect of the invention a polynucleotide is provided encoding a TBF protein or a chimeric protein of the invention. In an embodiment, a polynucleotide is provided that encodes a TBF protein or chimeric protein comprising the amino acid sequence of SEQ ID NO. 5 or SEQ ID. NO. 6, respectively. In another embodiment, a polynucleotide is provided comprising a sequence of SEQ ID NO.1 or 3, or a sequence that hybridizes under moderate or high stringency to the sequence of SEQ ID NO. 1 or 3.

The invention also contemplates polynucleotides having substantial sequence identity to a nucleic acid sequence of SEQ ID NOs. 1 and 3, in particular having at least about 90%, preferably 95 to 99% sequence identity with a nucleic acid sequence of SEQ ID NO. 1 and 3.

The invention provides an isolated polynucleotide that encodes a component of a bioluminescence generating system and a TBF protein of the invention.

A polynucleotide of the invention may be incorporated in a vector. A vector of the invention may be operationally associated with a promoter element that allows for constitutive or inducible expression of the protein or chimeric protein encoded by the polynucleotide. A vector of the invention may comprise a polynucleotide encoding a chimeric protein of the invention, a promoter element and a multiple cloning site located upstream or downstream of the sequence encoding a TBF protein of the chimeric protein.

The invention also contemplates a host cell comprising a vector of the invention. In an embodiment, a recombinant cell is contemplated that expresses heterologous polynucleotides encoding a TBF protein or chimeric protein of the invention under the control of a promoter element.

The vectors and host cells may be used to prepare a TBF protein or chimeric protein of the invention. In an aspect of the invention, a method for preparing a TBF protein is provided comprising (a) transferring a vector of the invention into a host cell; (b) selecting transformed host cells from untransformed host cells; (c) culturing a selected transformed host cell under conditions which allow expression of the protein; and (d) isolating the protein.

The invention provides a TBF protein or chimeric protein encoded by a polynucleotide of the invention.

In an aspect the invention provides a TBF protein or chimeric protein of the invention in combination with at least one component of a bioluminescence-generating system. In another aspect the invention provides a combination comprising a first composition containing a TBF protein or chimeric protein of the invention or mixtures thereof and a second composition containing a bioluminescence-generating system. Such a combination may be used for example with inanimate articles of manufacture.

A TBF protein or chimeric protein of the invention may be formulated into a composition. An embodiment of the invention provides a composition comprising a TBF protein or chimeric protein of the invention, and optionally at least one component of a bioluminescence-generating system.

The invention contemplates a complex comprising a TBF protein or a chimeric protein of the invention with a metal ("Luminescent complex"). In particular the molecule is capable of forming complexes through the modified CD-loop. In an embodiment, the molecule is a metal ion. The metal ion may be a lanthanide ion or analog or derivative thereof. Preferably the metal ion is a terbium ion. A complex comprising a TBF protein of the invention may be used in energy transfer between the complex and a luminescent agent acceptor (e.g. GFP).

In an aspect the invention provides a method for using a protein or composition of the invention to provide fluorescent illumination of novelty items or to detect and visualize tissue or infectious agents. A method is also provided for using a TBF protein, composition, or complex of the invention in an assay, immunoassay or an in vitro fluorescent-based screening assay.

In an embodiment, a method of the invention comprises contacting a sample with a TBF protein; exposing the sample to light at a first wavelength capable of electronic transition in the protein; and detecting an emission of light from the sample at a second wavelength that is longer than the first wavelength and results from a second electronic transition in the protein. In a particular embodiment, specific analytes in the sample are detected by coupling the protein to a reagent capable of selectively binding the analytes.

Therefore a method is providing for detecting analytes in a sample comprising: (a) coupling a TBF protein of the invention to a reagent capable of selectively binding the analytes; (b) contacting the sample with the TBF protein coupled to the reagent; (c) exposing the sample to light of an appropriate wavelength that excites the TBF protein; and (d) detecting luminescence thereby detecting analytes in the sample.

The proteins, compositions and complexes of the invention may be used to measure the distance between two atoms or assay an interaction between two atoms.

In an embodiment, a method is provided for measuring the distance between a first atom and second atom or assaying the interaction between the first atom and second atom comprising: (a) coupling a Luminescent complex to the first atom, and a luminescent agent acceptor to the second atom; and (b) measuring the distance between the first and second atoms, or assaying the interaction of the first and second atoms. The first and second atoms may be on the same molecule.

In another embodiment, a method is provided for assaying interactions between a first and second molecule comprising: (a) contacting, in the presence of a lanthanide ion, a first molecule labelled with a TBF protein and a second molecule labelled with a luminescent agent acceptor to provide a reaction mixture; (b) exposing the reaction mixture to light at a first wavelength capable of exciting lanthanide bound to the TBF protein and transferring energy to the luminescent agent acceptor; (c) detecting luminescence of the first molecule, second molecule, and/or lanthanide at selected wavelengths, wherein detection of luminescence of the second molecule indicates an interaction between the first molecule and second molecule. The first wavelength may be selected so that it optimizes the signal-to-noise ratio of the lanthanide emission. In particular, the first wavelength may be selected so that it is capable of penetrating a cell and optimizing lanthanide emission.

The invention also provides a kit comprising a TBF protein or chimeric protein of the invention. In particular, a kit may comprise a first composition containing a TBF protein formulated for systemic administration, local, or topical application; and a second composition containing the components or remaining components of a bioluminescence generating system, formulated for systemic, topical or local administration depending upon the application; and instructions for administration.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1. Nucleotide sequence of TBF, EGFP and TBFEGFP. (FIG. 1A) (SEQ ID NO. 1) The TBF gene was synthesized by Operon Technologies Inc. The gene was designed so the gene product would bind $Tb^{3+}$ and have a greater stability than oncomodulin (OM), the protein after which the gene product is modeled. (FIG. 1B) (SEQ ID NO. 2) The EGFP gene is a mutant of the GFP gene so its gene product gives a single absorbance peak and enhanced fluorescence. (FIG. 1C) (SEQ ID NO. 3) The TBFEGFP gene is a fusion of the TBF and EGFP genes. This was done by removing the stop codon from the TBF gene and inserting the codon for threonine (highlighted) to ensure transcription remains in frame through to the EGFP gene.

FIG. 2. Amino acid sequence comparison of oncomodulin (OM) (SEQ ID NO. 4) and terbofluor (TBF) (SEQ ID NO. 5). The CD-loop (residues 51-62) and EF-hand (residues 90-101) are in bold as well as the tryptophan in position 47 of TBF. Nucleotide changes from oncomodulin to terbofluor are underlined.

FIG. 3. Amino acid sequences of TBFEGFP and EGFP. The CD-loop (residues 51-62) and EF-hand (residues 90-101) are in bold as well as the tryptophan in position 47 of the TBF portion of the TBFEGFP protein (SEQ ID NO. 6). The amino acid linker, threonine, is underlined and the three amino acids of EGFP which form the fluorophore cyclic peptide is in bold and underlined (SEQ ID NO. 7).

FIG. 7. The emission spectra of TBF, EGFP and TBFEGFP at 25° C. Protein concentrations were 162 nM in 10 mM Pipes; 100 mM KCl; pH 6.5 with a $Tb^{3+}$ to protein ratio of 2:1. Symbols are TBF without $Tb^{3+}$ (○) and with $Tb^{3+}$ (●), EGFP without $Tb^{3+}$ (□) and with $Tb^{3+}$ (■), and TBFEGFP without $Tb^{3+}$ (◇) and with $Tb^{3+}$ (◆). Excitation wavelengths were 285 nm (A) and 488 nm (B).

Figure 8:
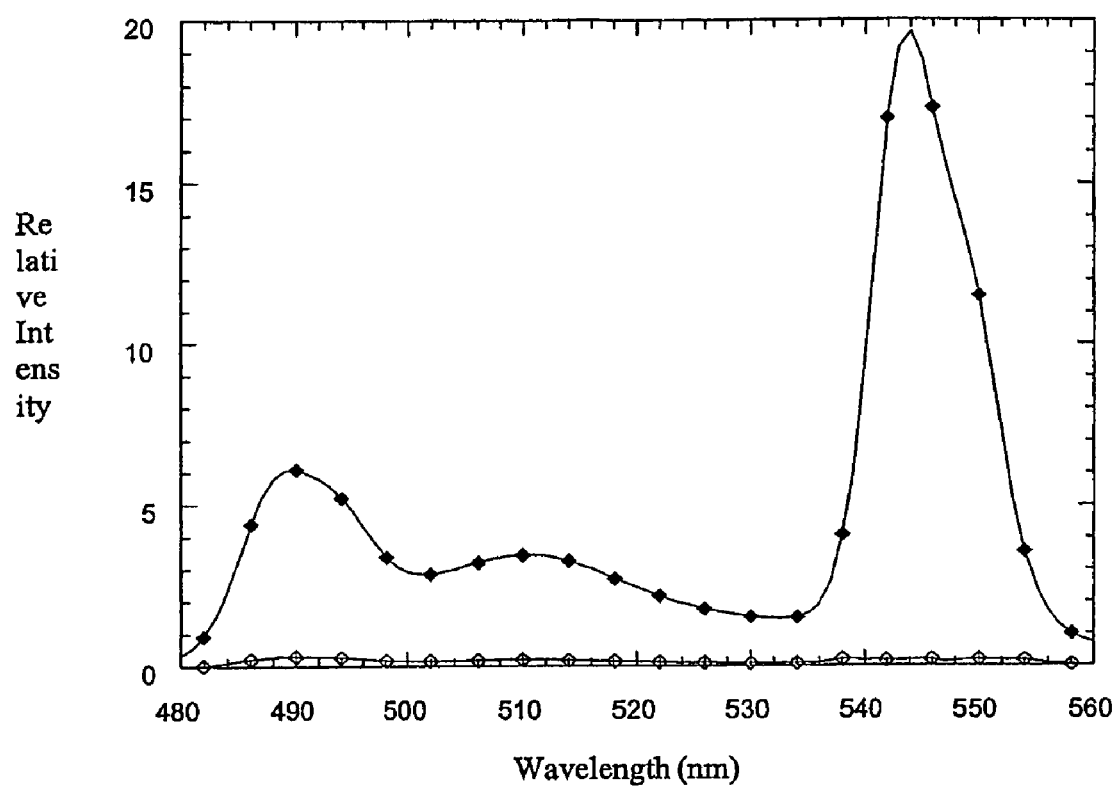

FIG. 8. The time-gated emission scans of TBFEGFP at 25° C. Protein concentrations were 5 μM in 10 mM Pipes; 100 mM KCl; pH 6.5 with a $Tb^{3+}$ to protein ratio of 2:1 for the spectrum with $Tb^{3+}$. Symbols are TBFEGFP without $Tb^{3+}$ (◇) and with $Tb^{3+}$ (◆). Excitation wavelength was 295 nm with a delay time of 0.2 msec and a 0.01 msec gate time.

Figure 9:
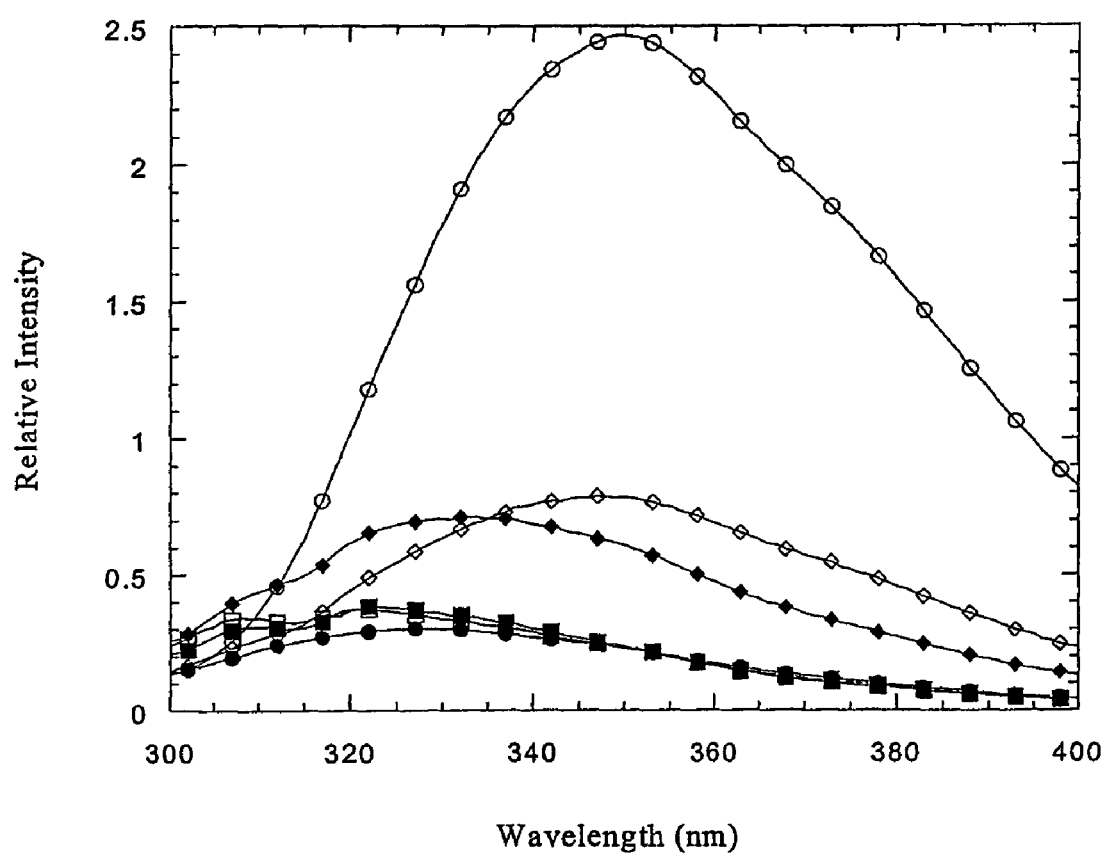

FIG. 9. Fluorescence spectra of the native and denatured states of TBF, EGFP, and TBFEGFP at 25° C. Excitation wavelength was 285 nm. Protein concentrations were 5.67 μM in 10 mM Pipes; 100 mM KCl; pH 6.5 for the native states and in 9.8 M urea for the denatured states. Terbium to protein ratio was 2:1 for TBF and TBFEGFP. Symbols are TBF native (○) and denatured (●), EGFP native (□) and denatured (■), and TBFEGFP native (◆) and denatured (◇).

Figure 10:
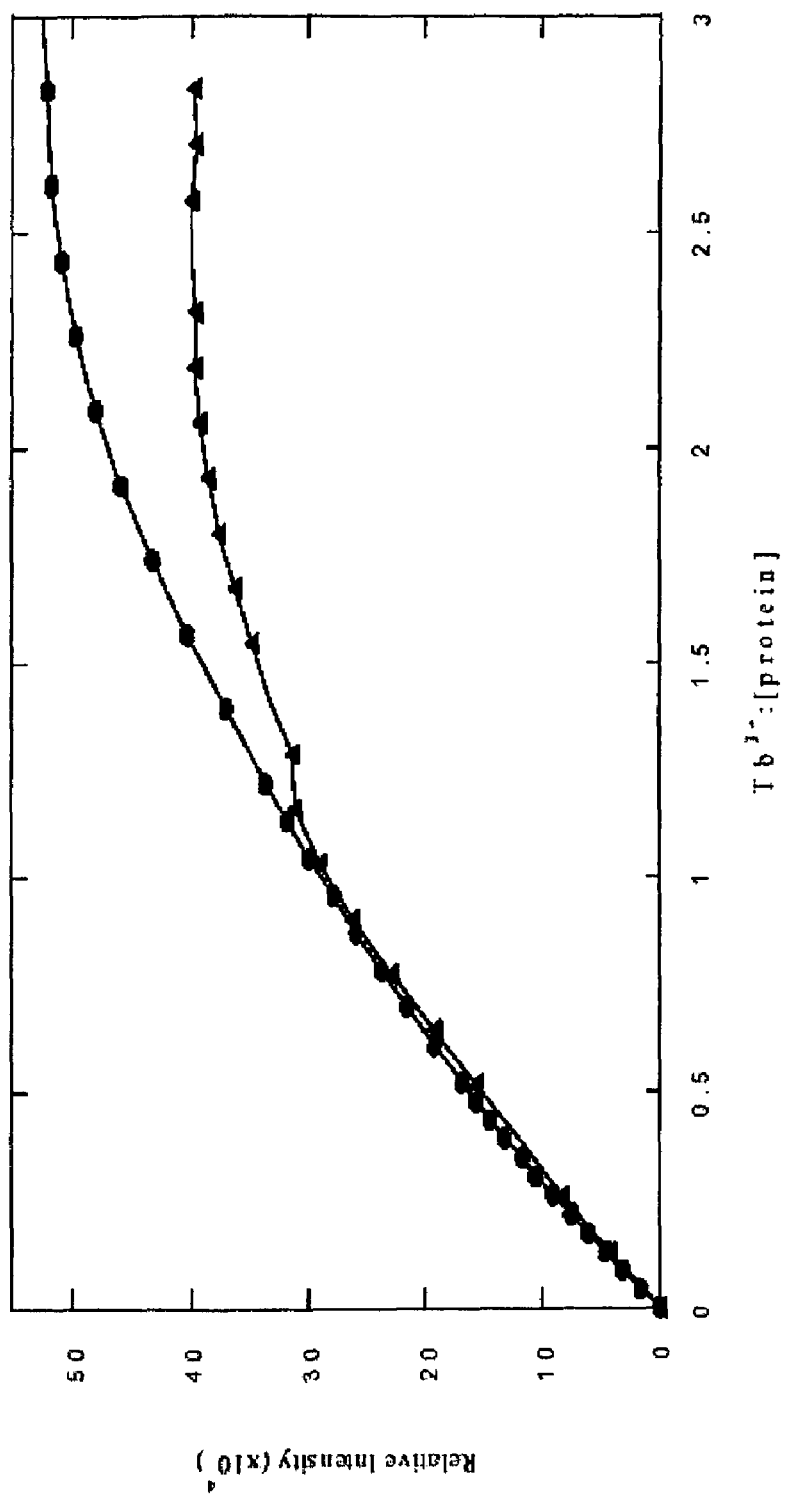

FIG. 10. The relative intensities of $Tb^{3+}$ fluorescence as $TbCl_3$ is titrated into TBF and CDOM33 at 25° C. Protein concentrations were 2 μM in 10 mM Pipes; 100 mM KCl; pH 6.5 buffer. Excitation and emission wavelengths were 295 nm and 545 nm, respectively. Symbols are TBF (●) and CDOM33 (▲).

FIG. 11. Amino acid sequence of TTE (SEQ ID NO. 8). The CD-loop (residues 51-62) and EF-hand (residues 90-101) are in bold as well as the tryptophan in position 47 of the TBF portion of the TTE protein. The TEV protease recognition site is in italics and bold. There are 4 glycines flanked on both sides of the recognition site to ensure access by the protease. The amino acid linker, threonine, is underlined and the three amino acids of EGFP which form the fluorophore cyclic peptide is bold and underlined.

Figure 12:
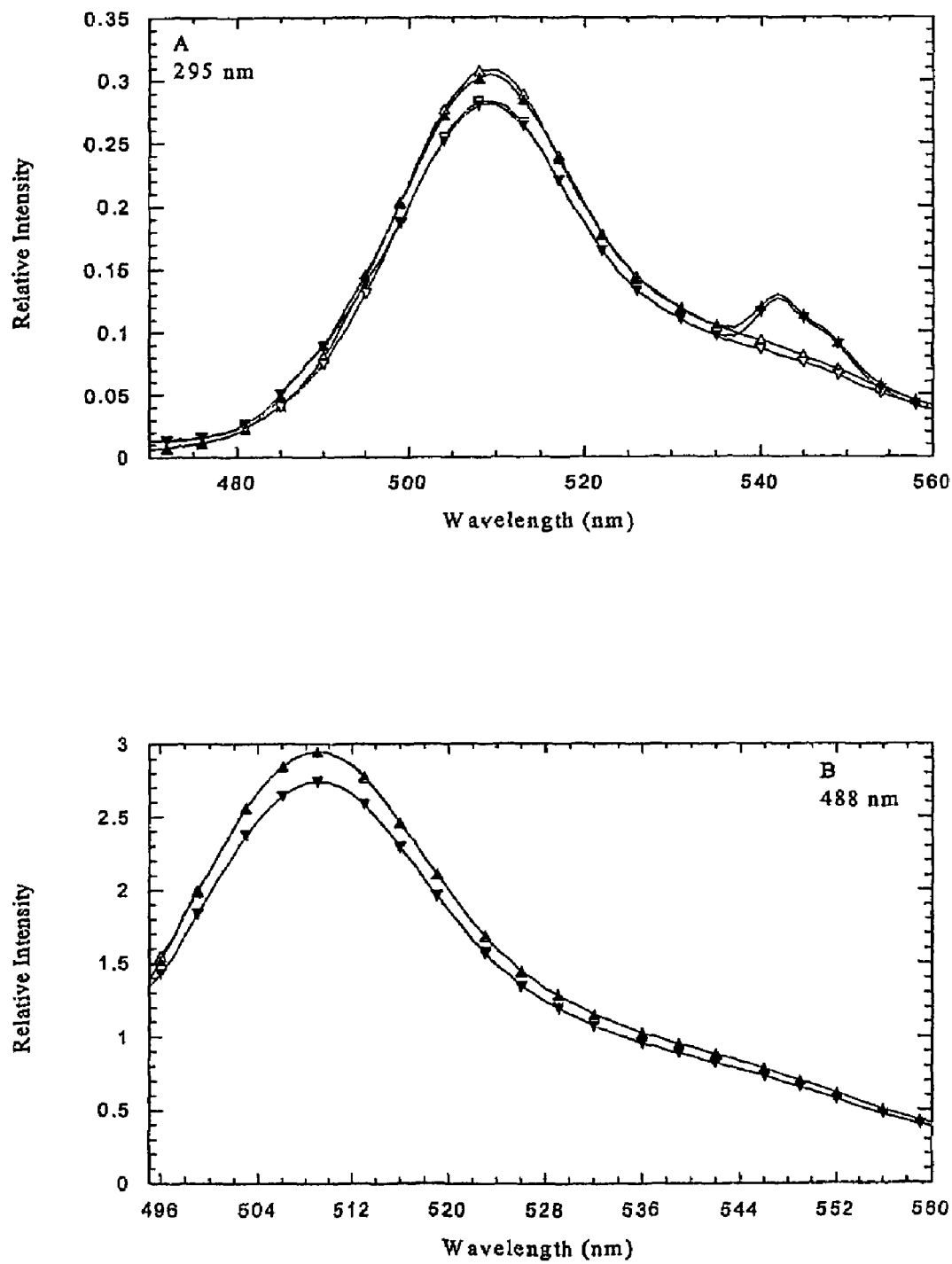

FIG. 12. The steady state emission spectra of TTE, cleaved and uncleaved at 25° C. Protein concentrations were 227 nM in 10 mM Pipes; 100 mM KCl; pH 6.5. Symbols are TTE without $Tb^{3+}$ (Δ) and with $Tb^{3+}$ (▲) and cleaved TTE without $Tb^{3+}$ (□) and with $Tb^{3+}$ (▼). Excitation wavelengths were 295 nm (A) and 488 nm (B).

FIG. 13. The time-gated emission spectra of TTE, cleaved and uncleaved at 25° C. Protein concentrations were 227 nM in 10 mM Pipes; 100 mM KCl; pH 6.5. Symbols are (A) TTE without $Tb^{3+}$ (□) and with $Tb^{3+}$ (▲) and (B) cleaved TTE without $Tb^{3+}$ (□) and with $Tb^{3+}$ (▼). Excitaion wavelength was 295 nm with a delay time of 0.2 msec and a 0.01 msec gate time.

DESCRIPTION OF THE INVENTION

In accordance with the present invention there may be employed conventional fluorescence, computer, detection, chemistry and laboratory procedures and techniques employed in the art. Standard methods may be used for chemical synthesis, fluorescence, optics, molecular biology, microbiology, and recombinant DNA techniques, computer software and integration. Where appropriate chemical reactions, cell assays, and enzymatic reactions may be performed according to manufacturer's instructions. Such techniques and procedures are explained fully in the literature. See for example, Sambrook, Fritsch, & Maniatis, Molecular Cloning: A Laboratory Manual, Second Edition (1989) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. I. Freshney, ed. (1986); Immobilized Cells and enzymes IRL Press, (1986); and B. Perbal, A Practical Guide to Molecular Cloning (1984); Lakowicz, J. R. for molecular biology techniques; Lakowicz, J. R. Topics in Fluorescence Spectroscopy, (3 volumes) New York: Plenum Press (1991), and Lakowicz, J. R. Emerging applications of fluorescence spectroscopy to cellular imaging: lifetime imaging, metal-ligand probes, multi-photon excitation and light quenching. Scanning Microsc Suppl Vol. 10 (1996) pages 213-24, for fluorescence techniques; and Optical Waveguide Theory, Snyder & Love published by Chapman & Hall for general optical methods.

Glossary

The following definitions are provided to facilitate understanding of certain terms used herein.

As used herein, the amino acids, which occur in the various amino acid sequences appearing herein, are identified according to their well-known, three-letter or one-letter abbreviations. The nucleotides, which occur in the various polynucleotides appearing herein, are designated with the standard single-letter designations used routinely in the art.

The term "isolated" means altered "by the hand of man" from its natural state i.e. if it occurs in nature it has been changed or removed from its original environment, or both. Therefore, the term contemplates a polynucleotide or protein removed from its natural environment, purified or separated, or substantially free of cellular material or culture medium when produced by recombinant DNA techniques, or chemical reactants, or other chemicals when chemically synthesized. Preferably, an isolated polynucleotide or protein is at least 60% free, more preferably at least 75% free, and most preferably at least 90% free from other components with which they are naturally associated.

The term "polynucleotide" refers to any polyribonucleotide or polydeoxyribonucleotide and is intended to include modified or unmodified DNA, RNA, including mRNAs, DNAs, cDNAs, and genomic DNAs, or a mixed polymer, and can be either single-stranded, double-stranded or triple-stranded. For example, a polynucleotide may be a single-stranded or double-stranded DNA, DNA that is a mixture of single- and double-stranded regions, or single-, double- and triple-stranded regions, single- and double-stranded RNA, RNA that may be single-stranded, or more typically, double-stranded, or triple-stranded, or a mixture of regions comprising RNA or DNA, or both RNA and DNA. The strands in such regions may be from the same molecule or from different molecules. The DNAs or RNAs may contain one or more modified bases. For example, the DNAs or RNAs may have backbones modified for stability or for other reasons. Moreover, DNAs or RNAs comprising unusual bases, such as inosine, or modified bases, such as tritylated bases, to name a few examples, are polynucleotides, as the term is used herein. It will be appreciated that a great variety of modifications have been made to DNA and RNA that serve many useful functions known to those skilled in the art. The term "polynucleotide" embraces such chemically, enzymatically or metabolically modified forms of nucleic acids, as well the chemical forms of DNA and RNA characteristic of viruses and cells, including simple and complex cells. The term "polynucleotide" and in particular DNA or RNA, refers only to the primary and secondary structure and it does not limit it to any particular tertiary forms. The term also embraces short polynucleotides often referred to as oligonucleotides.

The term "protein" used herein generally refers to any polypeptide or peptide comprising two or more amino acids joined to each other by peptide bonds or modified peptide bonds. The term refers to both short chains (i.e. peptides, oligopeptides and oligomers) and to longer chains. Proteins may contain amino acids other than the 20 gene encoded amino acids. Proteins include those modified by natural processes (e.g. processing and other post-translational modifications) and by chemical modification techniques. The same type of modification may be present in the same or varying degree at several sites in a given protein and a protein may contain many modifications. Modifications may occur in the peptide backbone, the amino acid side-chains, and the amino or carboxyl termini. Examples of modifications include acetylation; acylation; ADP-ribosylation; amidation; covalent attachment of flavin, a heme moiety, a nucleotide or nucleotide derivative, a lipid or lipid derivative, or phosphotidylinositol; cross-linking; cyclization; disulfide bond formation; demethylation, formation of covalent cross-links; glycosylation; hydroxylation; iodination; methylation; myristoylation; oxidation; proteoytic processing; phosphorylation; racemization; lipid attachment; sulfation, gamma-carboxylation of glutamic acid residues; and hydroxylation [By way of example see Proteins-Structure and Molecular Properties $2^{nd}$ Ed., T. E. Creighton, W.H. Freeman and Company, New York (1993), and Wold, P., Posttranslational Protein Modifications: Perspectives and Prospects, pages 1-12 in Posttranslational Covalent Modification Of Proteins, B. C. Johnson, Ed. Academic Press, New (1983); Seifer et al., Meth. Enzymol 182:626 (1990); and Rattan et al., Protein Synthesis: Posttranslational Modifications and Aging, Ann. N.Y. Acad. Sci. 663:48 (1992)]. The polypeptides may be branched or cyclic, with or without branching.

"Variant(s)" as used herein refers to a polynucleotide or protein that differs from a reference polynucleotide or protein respectively, but retains essential properties. A typical variant of a polynucleotide differs in nucleotide sequence from another polynucleotide. Changes in the nucleotide sequence of the variant may or may not alter the amino acid sequence of an encoded polypeptide. Nucleotide changes may result in amino acid substitutions, additions, deletions, fusions and truncations in the protein encoded by the reference sequence. A typical variant of a protein differs in amino acid sequence from another reference protein. Differences are generally limited so that the sequences of the reference protein and the variant are very similar overall and, in many regions, identical. A variant may differ in amino acid sequence by one or more substitutions, additions, and deletions in any combination. A substituted or inserted amino acid residue may or may not be one encoded by the genetic code. Mutagenesis techniques, direct synthesis, and other recombinant methods known to skilled artisans may be used to produce variants of polynucleotides and proteins.

"Vector" (or plasmid) refers to discrete elements that are used to introduce heterologous DNA into cells for either expression or replication thereof Selection and use of such vehicles are well within the skill of the artisan. An expression vector includes vectors capable of expressing DNAs that are operationally associated with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of TBF proteins or chimeric TBF proteins are those that are expressed in bacteria such as those described herein.

A "promoter element" or "promoter" refers to a segment of DNA or RNA that controls transcription of the DNA or RNA to which it is operationally associated. A promoter element includes specific sequences sufficient for RNA polymerase recognition, binding and transcription initiation. This portion of the promoter element is referred to as the promoter. In addition, the promoter element includes sequences that modulate this recognition, binding and transcription initiation activity of RNA polymerase. The sequences may be cis acting or may be responsive to trans acting factors. Promoters, depending upon the nature of the regulation, may be constitutive or regulated.

As used herein, "operationally associated" refers to the functional relationship of DNA with regulatory and effector sequences, such as promoters, enhancers, transcriptional and translational stop sites, and other signal sequences. For example, association of DNA with a promoter refers to the physical and functional relationship between the DNA and the promoter such that the transcription of the DNA is initiated from the promoter by an RNA polymerase that specifically recognizes, binds to and transcribes the DNA. In order to optimize expression and/or in vitro transcription, it may be necessary to remove, add or alter 5' untranslated sequences to eliminate potential inappropriate alternative translation initiation (i.e., start) codons or other sequences that may interfere with or reduce expression, either at the transcription or translation level. Alternatively, consensus ribosome binding sites (see, e.g., Kozak (1991) J. Biol. Chem 266:19867-19870) may be inserted immediately 5' of the start codon and may enhance expression. The need for such modification may be empirically determined.

"Bioluminescence" refers to the emission of light by biological molecules (or synthetic versions or analogs thereof).

A "bioluminescence generating system" refers to a set of reagents required to carry out a bioluminescent reaction. Thus, the specific photoproteins, solvents and other reagents that may be required to complete a bioluminescent reaction form such a system. Therefore a bioluminescence generating system refers to any set of reagents that, under appropriate reaction conditions, yield bioluminescence. Appropriate reaction conditions refers to the conditions needed for a bioluminescence reaction to occur, such as pH, salt concentrations and temperature. In general, bioluminescence systems include a photoprotein, and one or more activators. A specific bioluminescence system may be identified by reference to a specific TBF protein or chimeric TBF protein. The system would also include the particular activators necessary to complete the bioluminescence reaction, such as a lanthanide oil. The TBF proteins and chimeric TBF proteins provided herein may be incorporated into bioluminescence generating systems and used, as appropriate, with a luminescent agent acceptor (e.g. GFP).

"Antibodies" include monoclonal or polyclonal antibodies, immunologically active fragments (e.g. a Fab or (Fab)$_2$ fragments), antibody heavy chains, humanized antibodies, antibody light chains, genetically engineered single chain FV molecules, chimeric antibodies, for example, antibodies which contain the binding specificity of murine antibodies, but in which the remaining portions are of human origin, or derivatives, such as enzyme conjugates or labeled derivatives.

Antibodies including monoclonal and polyclonal antibodies, fragments and chimeras, may be prepared using methods known to those skilled in the art. An isolated native or recombinant polypeptide may be utilized to prepare antibodies. See, for example, Kohler et al. (1975) Nature 256:495-497; Kozbor et al. (1985) J. Immunol Methods 81:31-42; Cote et al. (1983) Proc Natl Acad Sci 80:2026-2030; and Cole et al. (1984) Mol Cell Biol 62:109-120 for the preparation of monoclonal antibodies; Huse et al. (1989) Science 246:1275-1281 for the preparation of monoclonal Fab fragments; and, Pound (1998) Immunochemical Protocols, Humana Press, Totowa, N.J. for the preparation of phagemid or B-lymphocyte immunoglobulin libraries to identify antibodies. The antibodies may also be obtained from scientific or commercial sources.

"Complementary," when referring to two nucleotide sequences, refers to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. Two sequences of nucleotides may be considered complementary if they are capable of hybridizing, preferably with less than 25%, more preferably with less than 15%, even more preferably with less than 5%, most preferably with no mismatches between opposed nucleotides. Preferably the two molecules will hybridize under conditions of high stringency.

Appropriate stringency conditions which promote hybridization are known to those skilled in the art, or can be found in Current Protocols in Molecular Biology, John Wiley & Sons, N.Y. (1989), 6.3.1-6.3.6. Stringency of hybridization in determining percentage mismatch may be as follows:
  1) high stringency: 0.1.times.SSPE, 0.1% SDS, 65° C.
  2) medium stringency: 0.2.times.SSPE, 0.1.% SDS, 50° C.
  3) low stringency: 1.0.times.SSPE, 0.1% SDS, 50° C.
    Equivalent stringencies may be achieved using alternative buffers, salts and temperatures.

The term "substantially" identical or homologous or similar varies with the context as understood by those skilled in the relevant art and generally means at least 70%, preferably at least 80%, more preferably at least 90%, and most preferably at least 95%, 96%, 97%, 98%, or 99% identity.

"Identity," as known in the art, is a relationship between two or more protein sequences or two or more polynucleotide sequences, as determined by comparing the sequences. "Identity" also refers to the degree of sequence relatedness between protein or polynucleotide sequences as determined by the match between strings of such sequences. "Identity" may be calculated by conventional methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Gri H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48. 1073 (1988). Methods to determine identity are designed to give the highest match between the sequences tested. Methods to determine identity are codified in publicly available computer programs. Examples of computer program methods to determine identity between two sequences include, but are not limited to, the GCG program package (Devereux, J., et al., Nucleic Acids Research 12(1). 387 (1984)), BLASTP, BLASTN, and FASTA (Atschul, S. F. et al., J. Molec. Biol 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403410 (1990). The Smith Waterman algorithm known in the art may also be used to determine identity.

Parameters for comparison of polypeptide sequences include the following: (1) Algorithm Needleman and Wunsch, J. Mol Biol. 48: 443-453 (1970); (2) Comparison matrix: BLOSSUM62 from Hentikoff and Hentikoff, Proc. Natl. Acad. Sci. USA. 89:10915-10919 (1992); (3) Gap Penalty: 12; and (4) Gap Length Penalty: 4. A useful publicly available program with these parameters is the "gap" program from Genetics Computer Group, Madison Wis. The above-mentioned comparison parameters are the default parameters for peptide comparisons (along with no penalty for end gaps).

Parameters for comparison of polynucleotide sequences include the following: (1) Algorithm: Needleman and Wunsch, J. Mol Biol. 48: 443-453 (1970); (2) Comparison matrix: matches=+10, mismatch=0; (3) Gap Penalty: 50; and (4) Gap Length Penalty: 3. The "gap" program from Genetics Computer Group, Madison, Wis. is a publicly available program with these default parameters for nucleic acid comparisons.

"Luminescent agent acceptor" refers to a substance that is capable of accepting energy from a luminescent protein or Luminescent complex of the invention. In an embodiment, the luminescent agent acceptor is a chromoprotein or photoprotein. In a preferred embodiment, the luminescent agent acceptor is a green fluorescent protein.

"Green fluorescent proteins (GFP)" refers to a class of chromoproteins found only among certain bioluminescent coelenterates. GFPs have been purified (Prasher et al, 1992, Gene 111:229-233) and cloned (PCT WO95/07463). GFPs include those isolated from the jellyfish species *Aequorea*, particularly *Aequorea victoria* (*A. victoria*) and *Aequorea forskalea* (Ward et al. (1982) Biochemistry 21:4535-4540; Prendergast et al. (1978) Biochemistry 17:3448-3453). *A. victoria* GFP is a monomeric protein that absorbs blue light with excitation wavelength maximum of 395 nm, with a minor peak at 470 nm, and emits green fluorescence with an emission wavelength of about 510 nm and a minor peak near 540 nm (Ward et al. (1979) Photochem. Photobiol. Rev 4:1-57).

Variants of GFP are preferably selected for use in the present invention. Examples of GFP variants include a variant having a Ser65Thr mutation of GFP (S65T) that has longer wavelengths of excitation and emission, 490 nm and 510 nm, respectively, compared to wild-type GFP (400 nm and 475 nm); a blue fluorescent variant of GFP (e.g. Y66H-GFP) (Heim et al, Proc. Nail. Acad. Sci. 91:12501, 1994), MmGFP (M. Zemicka-Goetz et al, Development 124:1133-1137, 1997) enhanced GFP ("EGFP") (Okabe, M. et al, FEBS Letters 407:313-319, 1997; Clontech, Cal.), or a red shifted variant, EYFP (yellow fluorescent protein excitation max. 513 nm). Other GFP variants are described on the worldwide web at the Structural Classification of Proteins site.

In an embodiment of the invention, the GFP is EGFP which has a Phe to Leu mutation at position 64 resulting in the increased stability of the protein at 37° C. and a Ser to Thr mutation at position 65 resulting in an increased fluorescence. EGFP commercially available from Clontech incorporates a humanized codon usage rendering it "less foreign" to mammalian transcriptional machinery and ensuring maximal gene expression. The coding sequence of Clontech's EGFP contains over 190 silent mutations that create a humanized open reading frame. Additionally sequences upstream of the EGFP have been converted to a Kozak consensus ribosome binding site, allowing for more efficient translation of the mRNA in mammalian cells.

"Enzyme recognition site" refers to a site which is recognized by an enzyme and which is preferably cleaved by the enzyme. An example of an enzyme recognition site is a protease recognition sequence, in particular a TEV protease recognition sequence, preferably ENLYFQG (SEQ ID NO. 14). The polynucleotide sequence ACCCTGAAAATACAAATTCTC (SEQ ID NO. 15) encodes a TEV recognition sequence. "Oncomodulin" refers to a small protein with 108 residues and a molecular weight of 11700 Da, which was originally isolated from rat hepatonias. Oncomodulin is classified as a parvalbumin-like protein based on its primary structure, and it belongs to the EF-Hand calcium-binding family. The sequences of such proteins possess six stretches of α-helices, lettered A through F. The latter four helices flank two functional metal binding loops known as the CD- and EF-binding loops (J. P. MacManus, Cancer Res. 39 (1979) 3000; D. Bemaert, et al 3. Cancer 43(1989) 719; J. P. MacManus et al, Eur. J. Biochem 136 (1983) 9; and W. C. Barker et al, Atlas of Protein Sequences and Structure, 1978 p. 273). "CDOM33" refers to a modified oncomodulin where the CD loop is changed from DNDQSGYLDGDE (SEQ ID NO. 12) to DMNAGDWIEFEE (SEQ ID. NO. 16) (MacManus et al J. Biol. Chem. 265: 10358-10366, 1990)

Embodiments of the Invention

Applicants have produced an oncomodulin mutant that has been modified from CDOM33 by substituting a phenylalanine (Phe) for a tryptophan (Trp) at position 47. The modification caused the Tb (III) luminescence to be enhanced by 17% for the protein relative to CDOM33. The protein, sometimes referred to as Terbofluor, is also extremely thermostable. Terbofluor was also conjugated to green fluorescent protein (TBF-EGFP). GFPs are able to fuse to many proteins via the N- or C-terminus and undergo energy transfer in vitro. Lantlianides have long-lived lifetimes which make them amenable to studies utilizing time-gating methods. The lifetime values for holo TBF and holo TBF-EGFP were found to be 2.54 ms and 2.52 ms, respectively. By employing time-gated detection, it is possible to witness a 16-fold signal enhancement of EGEP fluorescence due to the sensitisation of GFP by the 490 nm peak of Tb (III). TBF-EGFP was further engineered to contain the TEV protease recognition sequence (ENLYFQG (SEQ ID NO. 14)) between TBF and EGFP (herein referred to as "TTE".) An assay was also developed to assess the energy transfer to the EGFP by Tb (III). This was done by monitoring the enzymatic cleavage by TEV protease at the TEV recognition site (between Q and G) in order to abolish the sensitisation seen by Tb (III) to EGFP energy transfer system.

Therefore, in an aspect the invention provides a TBF protein in which the CD-loop of oncomodulin is replaced with a more potent metal binding site, and Phe47 is replaced with Trp47. The TBF protein may also be characterized as follows:

(a) Gln27 of oncomodulin is replaced with Lys27, (b) Ser36 of oncomodulin is replaced with Lys36, (c) extended C-terminus, and (d) greater thermal stability than oncomodulin. A TBF protein may also be characterized as having long-lived luminescence and a large Stoke's shift with long wavelength emission. In an embodiment, the CD loop is replaced with DKNADGWIEFEE (SEQ ID NO. 13).

In an aspect of the invention, a TBF protein is provided comprising an amino acid sequence of SEQ ID NO. 5. In addition to proteins comprising an amino acid sequence as shown in SEQ. ID. NO. 5, the proteins of the present invention include truncations, analogs, variant, and proteins having substantial sequence identity or similarity to a sequence of SEQ ID NO. 5.

A TBF protein may be associated or conjugated with one or more other molecules, such as proteins, preferably to prepare chimeric TBF proteins. This may be accomplished, for example, by the synthesis of N-terminal or C-terminal fusion proteins. Molecules that may be conjugated or associated with a TBF protein include proteins and in particular luminescent agent acceptors and target peptides (e.g. enzyme recognition sites).

A TBF protein and a molecule may be associated or conjugated via a linker. A linker may be any chemical or biologic molecule compatible with the TBF protein and molecule. Preferably a linker maintains a certain minimum proximity between the TBF protein and molecule. Where the molecule is a luminescent agent acceptor a linker may be used to ensure efficient energy transfer between the TBF protein and acceptor.

A TBF protein and a luminescent agent acceptor may be associated or conjugated via a target peptide (e.g. an enzyme recognition site.)

In an aspect of the invention a chimeric TBF protein is provided comprising (a) TBF and a green fluorescent protein (GFP), (b) TBF and an enzyme recognition site (e.g. protease recognition site), or (c) TBF, GFP, and an enzyme recognition site. In particular, the green fluorescent protein is EGFP which is encoded by the sequence of SEQ ID NO. 2 or comprises the amino acid sequence of SEQ ID NO. 7.

In particular embodiments, the chimeric TBF proteins comprise SEQ ID NO. 6 (TBFEGRP) or SEQ ID NO. 8 (TTE).

The invention also relates to isolated polynucleotides that encode a TBF or chimeric TBF protein. Nucleic acid probes derived from polynucleotides of the invention are also provided. The polynucleotides and nucleic acid probes may contain at least about 14, preferably at least about 16, or, if desired, 20 or 30 or more, contiguous nucleotides of sequence of nucleotides encoding a TBF protein or chimeric TBF protein. The polynucleotides and nucleic acid probes derived therefrom can be labeled, if needed, for detection.

In an embodiment of the invention, polynucleotides are provided encoding a TBF protein comprising the amino acid sequence of SEQ ID NO. 5. In an embodiment, a polynucleotide comprises a sequence of nucleotides set forth in SEQ ID NO.1, or a nucleic acid molecule that hybridizes under moderate or high stringency to the sequence of nucleotides set forth in SEQ ID NO. 1.

A polynucleotide is provided encoding a TBF protein comprising the amino acid sequence of SEQ ID NO. 5 and a sequence encoding a GFP, in particular having the amino acid sequence of SEQ ID NO. 7. In an embodiment, the sequence encoding a GFP comprises the sequence of SEQ ID NO. 2.

In another embodiment of the invention, polynucleotides are provided encoding a chimeric TBF protein comprising the amino acid sequence of SEQ ID NO. 6 or 8. In an embodiment, a polynucleotide comprises a sequence of nucleotides set forth in SEQ ID NO.3, or a nucleic acid molecule that hybridizes under moderate or high stringency to the sequence of nucleotides set forth in SEQ ID NO. 3.

Also provided are isolated and purified polynucleotides that encode a component of a bioluminescence generating system and a TBF protein.

The invention also provides polynucleotides that exhibit substantial sequence identity with the polynucleotides of the invention. These polynucleotides may be produced by substituting codons that encode conservative amino acids. In an aspect of the invention, the polynucleotides exhibit at least about 90%, preferably 95 to 99% sequence identity with a nucleic acid sequence of SEQ ID NO. 1 or 3.

The polynucleotides of the invention can be modified by substitution of codons optimized for expression in selected host cells or hosts, such as humans and other mammals, or can be further mutagenized to alter the emission properties.

The invention particularly contemplates vectors that contain a polynucleotide of the invention preferably operationally associated with a promoter element that allows for constitutive or inducible expression of a TBF protein of the invention. The vectors are capable of expressing a protein of the invention in a wide variety of host cells.

Vectors for producing chimeric TBF proteins (e.g. TTE, or TBEFGP) are also contemplated. These vectors may comprise a promoter element and a multiple cloning site located upstream or downstream of the polynucleotide encoding TBF.

In specific embodiments of the invention the vector is a ptacTBF, pTBFEGP, or pTTE vector as described herein.

The invention also relates to host cells comprising a polynucleotide or vector of the invention. In an embodiment, a recombinant cell is contemplated that expresses heterologous polynucleotides encoding a TBF protein or chimeric TBF protein of the invention under the control of a promoter element.

Recombinant host cells that contain the polynucleotides may be produced by transfection with DNA encoding TBF or a chimeric TBF protein, or by introduction of RNA transcripts of DNA encoding a TBF protein or a chimeric TBF protein. The DNA may be introduced as a linear DNA fragment or may be included in an expression vector for stable or transient expression of the encoding DNA.

The invention contemplates bacterial, yeast, plant cells, insect cells, and mammalian host cells, and plasmids for expression of polynucleotides of the invention. It is preferred that host cells are selected to express functional TBF or chimeric proteins thereof that retain the ability to fluoresce and that are not toxic to the host cell.

In some embodiments host cells may also comprise a polynucleotide encoding a component of a bioluminescence generating system (e.g. luminescent agent acceptor such as a green fluorescent protein). In a preferred embodiment, the GFP is EGFP encoded by the sequence of SEQ ID NO.2 or comprising the amino acid sequence of SEQ ID NO 7.

The polynucleotides, vectors, and recombinant cells may be used to produce TBF proteins. Therefore, a method is provided for preparing a TBF protein of the invention utilizing the purified and isolated polynucleotides of the invention. In an embodiment a method for preparing a TBF Protein is provided comprising (a) transferring a vector of the invention into a host cell; (b) selecting transformed host cells from untransformed host cells; (c) culturing a selected transformed host cell under conditions which allow expression of the TBF protein; and (d) isolating the TBF Protein.

Methods for generating chimeric TBF proteins are also provided. These methods include linking DNA encoding a gene of interest (e.g. encoding a luminescent agent acceptor), or portion thereof, to DNA encoding a TBF coding region in the same translational reading frame. The encoded protein of interest may be linked in-frame to the amino- or carboxyl-terminus of the TBF protein. A linker (e.g. one or more amino acids) may be used to link the proteins to ensure in-frame transcription, to maintain a certain proximity between the TBF protein and protein encoded by the gene of interest, or in some cases to ensure efficient energy transfer from the TBF protein to the protein encoded by the gene of interest. The DNA encoding the chimeric protein is operationally associated with a promoter element of a suitable expression vector. Alternatively, the promoter element can be obtained directly from the gene of interest and the promoter-containing fragment linked upstream of the TBF coding sequence to produce chimeric TBF proteins.

Cells that express a functional TBF protein may be used alone or in conjunction with a bioluminescence-generating system, in cell-based assays and screening methods, such as those described herein.

The invention also relates to the proteins encoded by the polynucleotides. In particular, purified TBF and chimeric TBF proteins, and compositions containing TBF and chimeric TBF proteins alone or in combination with at least one component of a bioluminescence-generating system are also provided. The TBF proteins and chimeric TBF proteins provided herein may be used in combination with any suitable bioluminescence generating system, but they are preferably used in combination with a green fluorescent protein system.

Antibodies, polyclonal and monoclonal antibodies that specifically bind to a TBF protein or chimeric protein of the invention or any of the proteins encoded by the polynucleotides of the invention are contemplated. These antibodies, monoclonal or polyclonal, can be prepared employing standard techniques, known to those of skill in the art. In particular, immunoglobulins or antibodies obtained from the serum of an animal immunized with a substantially pure preparation of a TBF protein or chimeric TBF protein are provided herein or an or epitope-containing fragment thereof is provided. Monoclonal antibodies are also provided. The immunoglobulins that are produced have, among other properties, the ability to specifically and preferentially bind to and/or cause the immunoprecipitation of a TBF protein or chimeric TBF protein, that may be present in a biological sample or a solution derived from such a biological sample.

The invention also contemplates compositions containing a TBF protein or chimeric TBF protein. A composition may take any of a number of forms, depending on the intended method of use therefor. A composition may be a solution, a suspension, liquid, powder, a paste, aqueous, non-aqueous, or any combination thereof. In certain embodiments, for example, the compositions contain a TBF protein or chimeric TBF protein formulated for use in luminescent novelty items, immunoassays, fluorescent energy transfer assays, fluorescent resonance energy transfer assays, HTRF homogeneous time-resolved fluorescence assays, or used in conjunction with multi-well assay devices containing integrated photodetectors.

The TBF proteins and chimeric proteins of the invention are capable of forming complexes with metals in particular through the modified CD-loop of the TBF protein ("Luminescent complex"). The metals may be luminescent analogs of calcium. Examples of metals that form complexes with proteins of the invention include lanthanides or analogs thereof. Lanthanides include europium, terbium samarium, and dysprosium. In an embodiment, a TBF protein or chimeric protein forms a complex with a lanthanide ion such as $Tb^{3+}$ or $E^{3+}$. Solutions of protein-lanthanide complexes are capable of intense luminescence. In addition to binding to a CD-loop, a lanthanide may bind to an EF binding site of a TBF protein or chimeric TBF protein of the invention.

TBF proteins, complexes, and chimeric proteins may be coupled to a wide variety of molecules to create specific labels, probes, diagnostic and/or therapeutic reagents, etc. Useful labelled molecules include peptides, proteins, antibodies, nucleotides, nucleosides, oligonucleotides, nucleic acid polymers, carbohydrates, lipids, and non-biological polymers or materials. The proteins and complexes of the invention may be used to label a cell or component thereof, a cellular system, a cellular fragment, or subcellular particle, including but not limited to viruses and bacteria and components thereof, and biological cells (e.g. animal, plant, insect, and yeast) and components thereof.

A TBF protein, chimeric protein, or complex may also comprise a targeting sequence to target a TBF protein to a particular cell, organelle, tissue, organ, molecule or analyte in a sample. For example, a TBF protein may be coupled to a reagent that selectively binds to an analyte to be detected in a sample.

TBF proteins, chimeric proteins, and complexes are useful as detectable labels in a wide variety of applications. Methods may involve contacting a sample portion with a luminescent protein or complex; exposing the sample portion to light at a first wavelength capable of electronic transition in the protein; and detecting an emission of light from the sample portion at a second wavelength that is longer than the first wavelength and results from a second electronic transition in the protein. Specific analytes in the sample may be detected by coupling the protein to a reagent capable of selectively binding the analyte.

An aspect of the invention provides a method for detecting analytes in a sample comprising: (a) coupling a TBF protein of the invention to a reagent capable of selectively binding the analytes; (b) contacting the sample with the TBF protein coupled to the reagent; (c) exposing the sample to light of an appropriate wavelength that excites the TBF protein; and (d) detecting luminescence thereby detecting analytes in the sample.

The TBF proteins, chimeric TBF proteins, and complexes of the invention have advantageous application in all areas in which luminescent markers are used. For example, they may be used to purify and/or label a species (typically molecules) of interest, detect luminescence energy transfer, detect dissociation and/or association of a molecule or molecules of interest, detect a conformational change in a molecule of interest, and detect an analyte.

The proteins, compositions and complexes of the invention can be used to provide fluorescent illumination of novelty items or they can be used in methods of detecting and visualizing tissue (e.g. neoplastic tissue), detecting infectious agents using immunoassays, such as homogenous immunoassays and in vitro fluorescent-based screening assays, (e.g. using multi-well assay devices), or provided in kits for carrying out one of these methods.

The proteins, compositions, and complexes of the invention can be used to obtain useful information about the structure, conformation, relative location, and/or interaction of molecules.

A Luminescent complex of the invention may find use in energy transfer between the complexes and a luminescent agent acceptor. In an aspect, the TBF proteins of the invention find use in non-radioactive energy transfer reactions using GFPs [see, International PCT application Nos. WO 98/02571 and WO 97/28261].

By coupling a Luminescent complex (e.g. protein-lanthanide complex donor) to one atom and a luminescent agent acceptor to a second atom, the distance between two atoms can be measured, or the interaction of the two atoms can be assayed. Where the atoms are on the same molecule, the method can provide useful information about the structure or conformation of a molecule. For example, the methods are used to monitor the status of a polymerase chain reaction by coupling the donor and acceptor to separated atoms of a diagnostic oligonucleotide. Where the atoms are on different molecules, the methods may provide useful information on the interactions or relative locations of the two molecules.

In particular luminescence energy transfer may be used to detect physical proximity of two molecules. To measure physical proximity of two molecules a TBF protein is attached to one molecule and a luminescent agent acceptor is attached to the other. The labelled molecules are combined and the TBF protein is excited by light of an appropriate wavelength. If the acceptor is sufficiently close to the TBF protein, energy will be transferred and the acceptor will emit light. A decrease in luminescence transfer energy and lifetime and an increase in luminescence transfer energy are quantifiable indices of physical proximity between the molecules.

Thus, the invention contemplates a method of detecting energy transfer in a sample comprising: (a) contacting the sample with a TBF protein associated with a metal ion (i.e. a Luminescent complex) and a luminescent agent acceptor; (b) illuminating the sample at a wavelength suitable for excitation of the TBF protein associated with the metal ion; and (c) measuring the amount of luminescence energy transfer from the TBF protein associated with the metal ion to the luminescent agent acceptor. Step (c) may comprise measuring a decrease or an increase in energy transfer. The TBF protein may be bound to a first molecule and the luminescent agent acceptor may be bound to a second molecule such that luminescence energy transfer occurs between the TBF protein and acceptor, and the method may further comprise the step of correlating the amount of luminescence energy transfer with the association of the first and second molecules. The TBF protein may be bound to a first portion of a molecule and the luminescent agent acceptor may be bound to a second portion of the molecule such that luminescence energy transfer occurs between the TBF protein and acceptor, and the method may further comprise correlating the amount of luminescence energy transfer with the dissociation of the first and second portions.

The invention also provides a method of detecting dissociation of a species comprising: (a) providing a species that is labelled with a TBF protein associated with a metal ion and a luminescent agent acceptor such that luminescence energy transfer occurs between the TBF protein and the acceptor; (b) exposing the species to a condition that is capable of dissociating the species such that the TBF protein and acceptor are no longer capable of luminescence energy transfer; (c) illuminating the species at a wavelength suitable for excitation of the TBF protein associated with the metal ion; (d) measuring an amount of luminescence energy transfer from the TBF protein associated with the metal ion to the acceptor; and (e) correlating the amount of luminescence energy transfer from the TBF protein to the acceptor with the dissociation of the species.

In an aspect of the invention a method is provided for assaying interactions between molecules (e.g. proteins) comprising: (a) contacting, in the presence of a lanthanide, a first molecule labelled with a TBF protein and a second molecule labelled with a luminescent agent acceptor (e.g. green fluorescent protein) to provide a reaction mixture; (b) exposing the reaction mixture to light at a first wavelength capable of exciting lanthanide associated with or bound to the TBF protein and transferring energy to the second molecule, (c) detecting luminescence of the first molecule, second molecule, and/or terbium at selected wavelengths, wherein detection of luminescence of the second molecule indicates an interaction between the first molecule and second molecule.

A method for assaying an interaction may also include in step (a) a test substance which potentially may modulate the interaction. A change in luminescence as compared to a control in the absence of the substance indicates that the substance is a modulator of an interaction. A test substance can be any substance, such as an inorganic compound, an organic compound, a protein, an antibody, a peptide, a carbohydrate, a lipid, or a combination thereof.

The first wavelength is selected so that it optimizes the signal-to-noise ratio of the lanthanide emission. Light sources include lasers (e.g. nitrogen, helium-cadmium, dye lasers, etc.) and arc lamps (e.g. high-pressure, mercury, xenon, quartz, etc.).

The above method may be a cell-based method and the molecules may be recombinantly expressed proteins. The first wavelength may be selected so that it is capable of penetrating the cell and optimizing lanthanide emission. In a preferred embodiment, photon excitation is utilized (e.g. 3× photon excitation).

The systems and cells provided herein can be used for high throughout screening protocols, intracellular assays, medical diagnostic assays, environmental testing, such as tracing bacteria in water supplies, in conjunction with enzymes for detecting heavy metals, in spores for testing autoclaves in hospital, foods and industrial autoclaves. Non-pathogenic bacteria containing the systems can be included in feed to animals to detect bacterial contamination in animal products and in meats.

The TBF proteins and chimeric TBF proteins, or cells that express them may be used in methods of screening for bacterial contamination and methods of screening for metal contaminants. To screen for bacterial contamination, bacterial cells that express the TBF protein and/or a luminescent agent acceptor (e.g. a green fluorescent protein) are put in autoclaves or in other areas in which testing is contemplated. After treatment or use of the area, the area is tested for the presence of glowing bacteria. Presence of such bacteria is indicative of a failure to eradicate other bacteria. Screening for heavy metals and other environmental contaminants can also be performed with cells that contain the polynucleotides of the invention provided herein, if expression is linked to a system that is dependent upon the particular heavy metal or contaminant.

Compositions that contain a TBF protein, chimeric TBF protein, or complexes of the invention, and optionally and at least one component of a bioluminescence-generating system, preferably a system using a green fluorescent protein are provided.

Combinations containing a first composition containing a TBF protein or chimeric TBF protein or mixtures thereof and a second composition containing a bioluminescence-generating system for use with inanimate articles of manufacture to produce novelty items are also provided These novelty items, which are articles of manufacture, are designed for entertainment, recreation and amusement, and include, but are not limited to: toys; finger paints and other paints; textiles; figurines; personal items, such as body lotions, gels, powders and creams, nail polishes, cosmetics including make-up, toothpastes and other dentifrices, soaps, cosmetics; crosslinked polyacrylamide containing a fluorescent protein and/or components of a bioluminescence generating system, which glow upon contact with water; items such as inks, paper; and foods.

Any article of manufacture that can be combined with a bioluminescence-generating system and provide entertainment, recreation and/or amusement is contemplated herein. As a result of the combination, the items glow or produce a glowing fluid or spray of liquid or particles.

The invention also contemplates methods for diagnosis and visualization of tissues in vivo or in situ using compositions containing a TBF protein optionally with a luminescent agent acceptor (e.g. green fluorescent protein). For example, a TBF protein can be used in conjunction with diagnostic systems that rely on bioluminescence for visualizing tissues in situ. The systems are particularly useful for visualizing and detecting neoplastic tissue and specialty tissue, such as during non-invasive and invasive procedures. The systems include compositions containing conjugates that include a tissue specific, particularly a tumor-specific, targeting sequence or agent linked to a TBF protein. The systems also include a second composition that contains one or more components of a bioluminescence generating reaction.

In an aspect, the diagnostic system includes two compositions. A first composition that contains conjugates that, in preferred embodiments, include antibodies directed against tumor antigens conjugated to a TBF protein. In certain embodiments, conjugates containing tumor-specific targeting agents are linked to a TBF protein. In other embodiments, tumor-specific targeting agents are linked to microcarriers that are coupled with, preferably more than one TBF protein. The second composition contains the remaining components of a bioluminescence generating system, typically a luminescent agent acceptor (e.g. green fluorescent protein). In some embodiments, these components, are linked to a protein carrier.

The invention also provides methods for diagnosing diseases, particularly infectious diseases, using chip methodology (see, e.g., copending U.S. application Ser. No. 08/990, 103) a bioluminescence-generating system with a TBF protein. In particular, the chip includes an integrated photodetector that detects the photons emitted by the bioluminescence-generating system.

In an embodiment, a chip is made using an integrated circuit with an array, (e.g. an X-Y array) of photodetectors. The surface of the circuit is treated so that it is inert to conditions of the diagnostic assays for which the chip is intended. A selected antibody or antibodies, such as an antibody specific for an antigen (e.g. bacterial antigen), is affixed to the surface of the chip above each photodetector. After contacting the chip with a test sample, the chip is contacted with a second antibody linked to a TBF protein or an antibody specific for the antigen that is linked to a component of a bioluminescence generating system. The remaining components of the bioluminescence generating reaction are then added. If any of the antibodies linked to a component of a bioluminescence generating system are present on the chip, light will be generated and detected by the photodetector. The photodetector is operatively linked to a computer, which is programmed so that it is capable of identifying the linked antibodies, recording the event, and thereby identifying antigens present in the test sample.

The invention also contemplates methods for identifying compounds using recombinant cells that express heterologous polynucleotides encoding a TBF protein or chimeric TBF protein under the control of a promoter element. The recombinant cells can be used to identify novel compounds or ligands that modulate the level of transcription from the promoter of interest by measuring TBF-mediated fluorescence. Recombinant cells expressing a TBF protein may also be used for monitoring gene expression or protein trafficking, or determining the cellular localization of the target protein by identifying localized regions of TBF-mediated fluorescence within the recombinant cell.

Other assays using the TBF proteins, complexes, or chimeric TBF proteins are contemplated herein. Any assay or diagnostic method known by those of skill in the art that employ green fluorescent protein are contemplated herein.

Kits containing the TBF proteins, complexes, chimeric TBF proteins, or compositions for use in methods, including those described herein, are provided. In one embodiment, the kits contain an article of manufacture and appropriate reagents for generating bioluminescence. Kits comprising bioluminescence generating reagents, including TBF proteins, chimeric proteins, complexes, or compositions of the invention are provided herein. The kits may be used for detecting and visualizing tissues (e.g. neoplastic tissues) and include a first composition that contains a TBF protein or chimeric protein and least one component of a bioluminescence generating system, and a second that contains the activating composition, which contains the remaining components of the bioluminescence generating system and any necessary activating agents.

Kits may include two compositions, a first composition containing the TBF protein formulated for systemic administration (or in some embodiments local or topical application), and a second composition containing the components or remaining components of a bioluminescence generating system, formulated for systemic, topical or local administration depending upon the application Instructions for administration will be included.

In other embodiments, the kits are used for the detection and identification of diseases, particularly infectious diseases, using multi-well assay devices and include a multi-well assay device containing a plurality of wells, each having an integrated photodetector, to which an antibody or panel of antibodies specific for one or more infectious agents are attached, and a composition containing a secondary antibody, such as an antibody specific for the infectious agent that is linked to a TBF protein or chimeric TBF protein. A second composition may also be employed comprising a bioluminescence generating system that emits a wavelength of light, which produces light that is detected by the photodetector to indicate the presence of the agent.

As noted above, fusions of nucleic acids encoding the chimeric proteins (e.g. TBF proteins with green fluorescent protein or a protease recognition site) are provided herein. A TBF protein and a protein such as a luminescent agent acceptor (e.g. GFP) may be linked via a target such as a peptide. These fusions in which the TBF and acceptor are linked via a target, such as a peptide, can be used as a tool to assess anything that interacts with the target. For example, the TBF proteins and green fluorescent protein may be linked via a target peptide which is an enzyme recognition site. In particular, the enzyme recognition site may be a protease recognition site, and the fusions are used to assess protease inhibitors.

In an aspect, a method is provided for assaying for inhibitors of an enzyme comprising: (a) reacting a chimeric TBF protein comprising a TBF protein fused to a luminescent agent acceptor via an enzyme recognition site which can be cleaved by the enzyme, and a test substance, in the presence of the enzyme, under conditions permitting cleavage of the enzyme recognition site by the enzyme; and (b) assaying for chimeric protein, TBF protein and/or luminescent agent acceptor. In an embodiment, a decrease in the amount of TBF protein and luminescent agent acceptor or an increase in chimeric protein compared to a control indicates that the test substance is an inhibitor. In a preferred embodiment, the enzyme is associated with a disease or condition and the substance is a potential therapeutic.

In an embodiment, a method is provided for assaying for protease inhibitors comprising: reacting a chimeric TBF protein comprising a TBF protein fused to a luminescent agent acceptor via a protease recognition site, and a test substance, in the presence of a protease, under conditions permitting cleavage of the protease recognition site by the protease; and assaying for chimeric protein, TBF protein, and/or luminescent agent acceptor. In an embodiment, a decrease in the amount of TBF protein and luminescent agent acceptor or an increase in chimeric protein compared to a control indicates that the test substance is an inhibitor.

In the above methods TBF protein, acceptor, and chimeric protein may be assayed by measuring luminescent energy transfer between the protein and acceptor.

Another aspect of the present invention provides a method of conducting a drug discovery business comprising:

(a) providing one or more systems for identifying agents by their ability to modulate (i.e. inhibit or potentiate) a molecular interaction or for identifying inhibitors of an enzyme associated with a disease or condition as described herein;

(b) conducting therapeutic profiling of agents identified in step (a), or further analogs thereof, for efficacy and toxicity in animals; and (c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The following non-limiting examples are illustrative of the present invention:

Example 1

Materials and Methods ptacTBF Construct

TBF is a variant of oncomodulin in which the CD loop has been modified to bind terbium (IE) as well as calcium (II) and an extended C-terminus for greater stability. The gene was synthesized by Operon Technologies, Inc. CA and designed so the gene would be flanked by EcoR I Hind III restriction sites for excise into other plasmids.

The gene was cut from the vector supplied by Operon Technologies and inserted into the pKK223-3 plasmid (Amersham Pharmacia Biotech) to take advantage of its tac promoter and the strong rrnB ribosomal terminator which stabilizes the plasmid by inhabiting read-through transcription initiated by the tac promoter. To do this, the vector containing the TBF gene and the pKK223-3 plasmid were both treated with the EcoR I and Hind III restriction enzymes (MBI Fermentas) at 37° C. for 2 hours and then run on a 1% agarose gel in TBE buffer to separate the fragments. The DNA was extracted from the gel using Ultra Clean Gelspin DNA purification kit from Mo Bio Laboratories.

Clonables by Novagen was used to ligate TBF into the pKK223-3 plasmid. The ligation was performed as per instructions supplied with the kit. The vector was renamed ptacTBF. The vector was then transformed into *E. coli* JM109 cells (Promega) by electroporation (Gene Pulser II by Bio-Rad). The cells were recovered with SOC medium, incubated for 40 minutes at 37° C. and plated on LB with 100 µg/ul AMP for selection.

To verify the ligation reaction and transformation, 5 ml of LB broth was inoculated with a colony and grown overnight, the DNA was extracted using Qiagen's Miniprep kit and sent for DNA sequencing.

pTBFEGFP Construct pTBFEGFP was constructed by fusing the TBF gene to the start of the EGFP gene. Primers were designed for the TBF gene to put a Pst I and a Nco I restriction site at the start and end of the gene, respectively, and remove the stop codon. An amino acid linker, threonine, was needed to ensure transcription remained inframe through to the EGFP gene. Primers were designed as follows: coding strand, 5'-CGCGCCATG-GTGGATTCAGCTACCATTTCTTGG-3' (Nco I site is in bold) (SEQ ID NO. 9); anticoding strand, 5'-GCGCCTG-CAGGATGAGCATTACCGATA-3' (Pst I site is in bold) (SEQ ID NO.10).

The gene was amplified with the restriction sites using PCR on a Robo Cylcer (Stratagene). The PCR product was cleaned using Qiaquick PCR purification kit by Qiagen.

A restriction digest of the PCR product and the pEGFP (Clontech) vector were both treated with Pst I and Nco I restriction enzymes (MBI Fermentas) at 37° C. for 2 hours and then run on a 1% agarose gel in TBE buffer to separate the fragments. The DNA was extracted from the gel using Ultra Clean Gelspin DNA purification kit from Mo Bio Laboratories.

To ligate the gene into the pEGFP vector, Clonables by Novagen was used. The ligation was performed as per instructions supplied with the kit. The vector was renamed pTBFEGFP. The vector was then transformed into *E. coli* JM109 cells (Promega) by electroporation (Gene Pulser II by Bio-Rad). The cells were recovered with SOC medium, incubated for 40 minutes at 37° C. and plated on LB with 100 ug/ul AMP for selection.

To verify the ligation reaction and transformation, 5 ml of LB broth was inoculated with a colony and grown overnight, the DNA was extracted using Qiagen's Miniprep kit and sent for DNA sequencing.

Purification of TBF, EGFP and TBFEGFP

The *E. coli* JM109 strain, transformed by ptacTBF, pEGFP and pTBFEGFP were each grown at 37° C. with aeration in terrific broth containing extra glycerol, casamino acids and AMP until log phase. At that time, additional terrific broth was added as well as IPTG for a final concentration of 1 mM IPTG. The cells continued to grow at 37° C. with aeration. The cells were harvested and washed in PMS buffer (10 mM Pipes; 10 mM NaCl; 10 mM $MgCl_2$; 100 mM KCl; pH 6.5), resuspended in PMS buffer and passed through an Emulsi-Flex Homogenizer (Avestin) to break open the cells and then each was collected in a flask. The crushed cells were heated in a hot water bath to 65° C. After 5 minutes, the flask were put on ice to cool and then centrifuged. The supernatants were collected, poured into dialysis tubing (3,500 MWCO for TBF and 12,000-14,000 MWCO for TBFEGFP and EGFP) and dialyzed against PMS buffer. The buffers were changed once with PMS buffer and twice with PLS buffer (10 mM Pipes; 10 mM NaCl; pH 6.5) during a 24 hour period. The supernatants were each loaded onto a DEAE column (Amersham Pharmacia Biotech) equilibrated with PMS buffer. A salt gradient was set up with the low salt being PLS buffer and the high salt being PHS buffer (10 mM Pipes; 510 mM NaCl; 10 mM $MgCl_2$; 100 mM KCl; pH 6.5). The elutions were monitored at 280 nm for tyyptophan absorbance. Fractions were collected and each protein was determined by denaturing gel electrophoresis, pooled, lyophilized, redissolved in a minimal amount of PMS buffer, and each was loaded onto a sizing column (Amersham Pharmacia Biotech) equilibrated with PMS buffer (G-50 for TBF and S-100 for EGFP and TBFEGFP). The elutions were again monitored at 280 nm for tyyptophan absorbance. Fractions were collected and each protein was determined by denaturing gel electrophoresis, pooled, dialyzed against dd$H_2O$, and lyophilized. Protein purity was judged by denaturing gel electrophoresis and mass spectrometry.

Mass Spectrometry

MDS Sciex Q-STAR mass spectrometer was used to verify the purity of TBF, EGFP and TBFEGFP as well as determine its molecular weight.

The proteins were each diluted to a concentration of 6 fmol/µl (based on the sum of the molecular weights of the non-ionized amino acids minus that of water) with 45% methanol: 3.75% formic acid. The methanol is used for its volatility and formic acid is used to install positive charges on the protein. The protonated proteins were each loaded onto a glass needle coated with gold and palladium and introduced into the mass spectrometer. All proteins were determined to be pure and have molecular weights of 12, 453.50±0.43, 26140.56±1.16 and 38,678.54±0.97 Daltons for TBF, EGFP, and TBFEGFP, respectively.

Titration of TBF and TBFEGFP with Terbium (III) Chloride

The titrations of TBF and TBFEGFP with $Tb^{3+}$ were performed on a PE C-61 (Photon Technology International) by adding small aliquots of $TbCl_3$ and monitoring the fluorescence at 490 nm with an excitation wavelength of 285 nm.

The concentrations of TBF were determined by absorbance spectroscopy with a Cary 300 Bio UV-Vis spectrophotometer equipped with a temperature control and stirring unit using a quartz cuvette of 1 cm pathlength. The extinction coefficients, $\epsilon$, for TBF and TBFEGFP were calculated by using the data from the Edelhoch method {Edelhoch 1967 1/id} with the equation $$\epsilon_{280} = a \cdot \epsilon_{Trp} + b \cdot \epsilon_{Tyr} + c \cdot \epsilon_{Cys} \qquad (1)$$

where $\epsilon_{280}$ is the extinction coefficient of the protein at 280 nm in $M^{1-}$ $cm^{1-}$, $\epsilon_{Trp}$, $\epsilon_{Tyr}$, and $\epsilon_{Cys}$ are the extinction coefficients at 280 nm of tryptophan (5690 $M^{1-}$ $cm^{1-}$), tyrosine (1280 $M^{1-}$ $cm^{1-}$) and cysteine (120 $M^{1-}$ $cm^{1-}$), respectively, and a, b and c are the number of each type of amino acid in the protein. The concentration of protein was calculated by using the equation $$C = \frac{Abs}{\varepsilon_{280} \cdot b} \qquad (2)$$

where C is the concentration in M, Abs is the absorbance and has no units, $\epsilon_{280}$ is the extinction coefficient at 280 nm in $M^{1-}$ $cm^{1-}$ as determined from equation 1, and b is the pathlength in cm.

Terbium titrations were recorded on a PTI C-61 fluorimeter equipped with a temperature control and stirring unit using a quartz cuvette of 1 cm pathlength. The protein concentration was 8.87 µM in 10 mM Pipes; 100 mM KCl; pH 6.5 buffer at 298 K and excited at a wavelength of 285 nm. Measurements were monitored at an emission wavelength of 490 nm at increasing terbium concentrations. The observed fluorescence was corrected for the contributions from the buffer and expressed as relative intensity with arbitrary units.

Lifetime Measurements

The lifetime measurement of TBF was recorded on a Spectromax Gemini fluorescent plate reader (Molecular Devices) at 25° C. The concentration of TBF was 135 nM in 10 mM Pipes; 100 mM KCl; pH 6.5 with a ratio of $Tb^{3+}$ to protein concentration of 2:1 and excited at a wavelength of 285 nm. Measurements were monitored at 545 nm with a cutoff filter of 455 nm and a PMT setting of high sensitivity. Two hundred µsecond windows were used for a total of eight windows where the measurements taken were at the mid point of each window. The observed fluorescence was corrected for the contributions from the buffer and expressed as relative intensity with arbitrary units.

As the Spectromax Gemini could not determine the lifetime of TBFEGFP, it was determined using an Eclipse (Varian, Inc.). The concentration of TBFEGFP was 135 nM in 10 mM Pipes; 100 mM KCl; pH 6.5 with a ratio of $Tb^{3+}$ to protein of 2:1 and excited at a wavelength of 295 nm. Measurements were monitored at 545 nm with a 0.2 msec time delay, 0.01 msec gate time for 5 msec.

The lifetime of the terbium (III) in TBF and TBFEGFP were determined by the equation $$RI = I_o e^{-t/\tau} \quad (3)$$

where RI is the relative intensity and represents the time-dependent intensity, $I_o$ is the intensity at time zero, t is the time, and $\tau$ is the lifetime of the fluorophore and equals the inverse of the decay rate. The lifetime of terbium (III) was determined to be 2.73±0.03 msec in TBF and 1.92±0.08 msec in TBFEGFP.

Steady State Excitation and Emission Spectra

Excitation and emission spectra were recorded on a PTI C-61 fluorimeter equipped with a temperature control and stirring unit using a quartz cuvette of 1 cm pathlength. Bandwidths for both excitation and emission were set at 4 nm. Protein concentrations were 162 nM. For protein scans with $Tb^{3+}$, the ratio of $Tb^{3+}$ to protein was 2:1. Excitation scans were performed at emission wavelengths of 490 nm and 545 nm ($Tb^{3+}$), and 510 nm (EGFP). Emission scans were performed at excitation wavelengths of 285 nm (for Trp) and 488 nm (EGFP). The observed fluorescence was corrected for the contributions from the buffer and expressed as relative intensity with arbitrary units.

Time-Gated Fluorescence Spectra

Time-gated fluorescence emission spectra were performed on an Eclipse fluorimeter (Varian, Inc.) equipped with a temperature control and stirring unit using a quartz cuvette of 1 cm pathlength. Bandwidths for both excitation and emission were set at 10 nm. Protein concentrations were 5 µM in 10 mM Pipes; 100 mM KCl; pH 6.5 buffer and the ratio of $Tb^{3+}$ to protein was 2:1 for the spectrum with $Tb^{3+}$. The excitation wavelength was set to 295 nm. The time gate window was set at 0.01 msec with a delay time of 0.2 msec. The observed fluorescence was corrected for the contributions from the buffer and expressed as relative intensity with arbitrary units.

Steady State Fluorescent Folding Spectra

Emission spectra were recorded on a PTI C-61 fluorimeter equipped with a temperature control and stirring unit using a quartz cuvette of 1 cm pathlength. The excitation wavelength was 285 nm at 25° C. with a bandwidth of 4 nm. Protein concentrations were 5.67 µM and the ratio of $Tb^{3+}$ to protein was 2:1 for TBF and TBFEGFP. The proteins were scanned between 300 nm and 400 nm to monitor tryptophan fluorescence. The observed fluorescence was corrected for the contributions from the buffer and expressed as relative intensity with arbitrary units.

Results

Design of TBF and TBFEGFP

Terbofluor (TBF) is modeled after rat β-parvalbumin (β-PV), also known as oncomodulin (OM), a small protein belonging to the "EF-Hand" calcium-binding family that includes calmodulin, troponin C, and calbindin. OM's CD and EF sites have shown they have different metal-binding affinities, with CD having an affinity for $Ca^{2+}$-binding and EF having an affinity for $Ca^{2+}$ and $Mg^{2+}$ {Henzl, Hapak, et al. 1986 25/id}. However, the lanthanide terbium $Tb^{3+}$, has been used extensively as a luminescent analogue of $Ca^{2+}$ to study structure-function relationships {MacManus, Hogue, et al. 1990 2/id} {Hogue, MacManus, et al. 1992 3/id} {Clark, Hill, et al. 1993 10/id} {Zheng, Hogue, et al. 1998 5/id} {Crescenzi, et al. 1998 6/id} {Stout, Zhou, et al. 1998 7/id} and binds to the CD and EF sites. For $Tb^{3+}$ fluorescence enhancement, the CD loop was changed from DNDQSGYLDGDE (SEQ ID NO. 12) to DKNADGWIEFEE (FIG. 2) (SEQ ID NO. 13). This particular sequence, with the Trp in the $7^{th}$ position of the loop and position 57 in the protein and given the name CDOM33, has been shown to enhance $Tb^{3+}$ luminescence {MacManus, Hogue, et al. 1990 2/id} {Zheng, Hogue, et al. 1998 5/id} by its close proximity to the metal ion, but it is the Trp in position 47 which further enhances $Tb^{3+}$ luminescence (FIG. 10). Phe in position 47 is buried within the hydrophobic core of the protein and situated in the cleft between the two binding sites and has been shown to have a greater sensitivity to metal ions in the CD site than other residues in the vicinity {Williams, Corson, et al. 1986 26/id}. Other changes to the protein, such as Gln-27 to Lys-27, Ser-36 to Lys-36, and the extended C-terminal mimics a hydrogen bonding network found in rat α-PV, another form of OM. In α-PV, the carboxylate of Ser-109 can form salt bridges and hydrogen bonds with side chains Lys-27, Gln-31 and Lys-36{McPhalen, Sielecki, et al. 1994 18/id}. These tertiary interactions are absent in the truncated C-terminal of OM. Also, the carboxylate of side chain Glu-108 forms a salt bridge with the $\epsilon\text{-NH}_3^+$ of Lys-27. These salt bridges and hydrogen bonding networks add thermal stability by resisting unfolding of the EF site {Corson, Williams, et al. 1986 27/id} {Ahmed, Rose, et al. 1993 17/id} {Henzl & Graham 1999 12/id}. The thermal stability of TBF is, by far, the most stable (Table 3).

The fusion protein, TBFEGFP, was designed to study fluorescence resonance energy transfer (FRET) from the $Tb^{3+}$ in the TBF domain to the chromophore in the EGFP domain. To fuse the two proteins, a linker was required to ensure inframe transcription (FIG. 1C). The linker encoded for the amino acid threonine and prevented the amino acid methionine from EGFP from being cleaved (FIG. 3) adding two more amino acids to the fusion protein than if they were two separate proteins.

Titrations with Terbium Chloride

Figure 4:
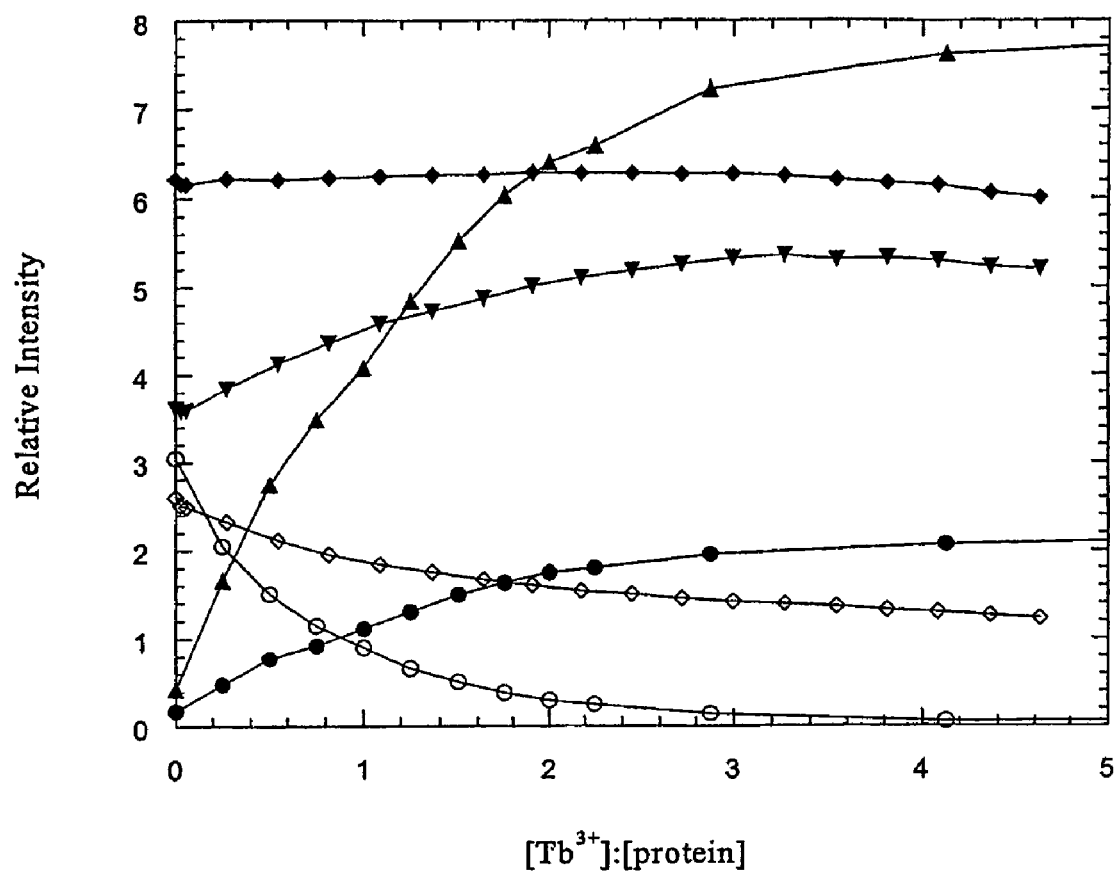
FIG. 4. The relative intensities of tryptophan and $Tb^{3+}$ fluorescence as $TbCl_3$ is titrated into TBF and TBFEGFP at 25° C. Protein concentrations for TBF and TBFEGFP were 3.37 μM in 10 mM Pipes; 100 mM KCl; pH 6.5 buffer. Excitation wavelength was 285 nm. Emission wavelengths were 350 nm: TBF (○) and TBFEGFP (◇), 490 nm: TBF (●) and TBFEGFP (♦) and 545 nm: TBF (▲) and TBFEGFP (▼). The maximum relative intensities for TBF and TBFEGFP occur at a $Tb^{3+}$ to protein concentration of 2:1 when monitoring the $Tb^{3+}$ fluorescence.

The relative intensities of fluorescence due to the binding of $Tb^{3+}$ to TBF and TBFEGFP are shown in FIG. 4. Results were obtained by the indirect excitation of $Tb^{3+}$ through Trp by exciting at 285 nm and monitoring at 350 nm for Trp fluorescence and 490 nm and 545 nm for $Tb^{3+}$ fluorescence.

The shapes of the curves for TBF show a steady increase in $Tb^{3+}$ fluorescence monitored at 490 nm and 545 nm and a decrease at 350 nm. The steady increase at 490 nm and 545 nm occurs as the binding sites for $Tb^{3+}$ become simultaneously occupied and an intensity maximum was reached once all the sites had been occupied by the lanthanide. This maximum intensity was reached when the $Tb^{3+}$ to protein concentration was 2:1 indicating binding of $Tb^{3+}$ to both the CD and EF binding sites. A greater increase in fluorescence was noted when monitored at 545 nm due to the transitions arising between the $^5D_4$ to $^7F_5$ states (490 nm) and the $^5D_4$ to $^7F_6$ states (545 nm) {Bhaumik & El-Sayed 1965 35/id}. Also, there is a decrease of ~83% in Trp fluorescence as $Tb^{3+}$ is added resulting from energy being transferred from Trp to the lanthanide. Energy transfer from Trp to lanthanides has been shown to enhance lanthanide luminescence {Horrocks & Sudnick 1979 33/id} {De Jersey, Jeffers, et al. 1981 32/id} {Brittain, Richardson, et al. 1976 31/id} and thereby decrease Trp fluorescence. In comparison (FIG. 10), titration of the CDOM33 protein with $Tb^{3+}$ showed an increase until the concentration of $Tb^{3+}$ to protein was 1:1 and then a second steady increase until the concentration of $Tb^{3+}$ to protein was 2:1 indicating one binding site becomes occupied before the other. Also, the maximum fluorescence reached with TBF was 17% greater than CDOM33 indicating that the Trp in position 47 does indeed increase $Tb^{3+}$ luminescence.

The shapes of the curves for TBFEGFP show a high fluorescence when monitored at 490 nm with no change. This is due to the peak being buried under the fluorescence peak of the EGFP's chromophore. The high fluorescence with a slight increase at 545 nm is due to the 545 nm peak being partially buried, so some increase is seen as $Tb^{3+}$ is added and a decrease at 350 nm due to the energy transfer to $Tb^{3+}$. However, there still is a fluorescence maximum when the $Tb^{3+}$ to protein concentration was 2:1. In both the TBF and TBFEGFP the CD and EF sites are occupied by $Tb^{3+}$. The EGFP fluorophore is a cyclic peptide formed posttranslationally with an excitation and emission maxima of 488 nm and 510 nm, respectively {Cody, Prasher, et al. 1993 37/id}{Heian, Prasher, et al. 1994 38/id}{Davis, Ward, et al. 1995 39/id}. EGFP has a high fluorescence at 510 nm as its extinction coefficient is 55, 900 $M^{1-}$ $cm^{1-}$ {Patterson, Knobel, et al. 1997 36/id}. The differences in maximum intensity between the TBF and TBFEGFP proteins are possibly due to a complex energy transfer system within the fusion protein. Here energy transfer is from the Trp to $Tb^{3+}$ in the TBF domain, from Trp to the EGFP chromophore in the EGFP domain, and from $Tb^{3+}$ in the TBF domain to the chromophore in the EGFP domain. There is also the possibility of a Dexter energy exchange system going on as has been observed in the past with proteins possessing $Tb^{3+}$ {Hogue, MacManus, et al. 1992 3/id} {MacManus, Hogue, et al. 1990 2/id}

Lifetime Measurements

As already stated, lanthanides as probes for studying structure-function relationships has been well established as they possess valuable properties as substitutes for $Ca^{2+}$ in proteins and remain in the excited state for long periods of time {Lakowicz 1983 29/id} {Horrocks & Sudnick 1979 33/id}. Terbium has an unpaired electron in the 4 f orbital which is shielded from external forces by the outer electrons of 5 $s^2$, 5 $p^6$ and 6 $s^2$. Terbium luminescence results from transitions between the $^5D_4$ to $^7F_6$ states giving a sharp peak at 490 nm and transitions from $^5D_4$ to $^7F_6$ states giving a sharp peak at 545 nm {Bhaumik & El-Sayed 1965 35/id}. Lifetimes of terbium have been measured between 0.6-1.9 msec {Selvin, Rana, et al. 1994 42/id} {Li & Selvin 1995 43/id} {Chen & Selvin 1999 9/id}, 100 nsec-10 μsec {Demas & DeGraff 1992 41/id}, and 0.2-0.4 msec {Sabbitini, Guardigli, et al. 1993 40/id} in aqueous solutions and up to 2.7 msec in deuterium {Chen & Selvin 1999 9/id} as compared to Trp with a lifetime of ~9.0 nsec.

Figure 5:
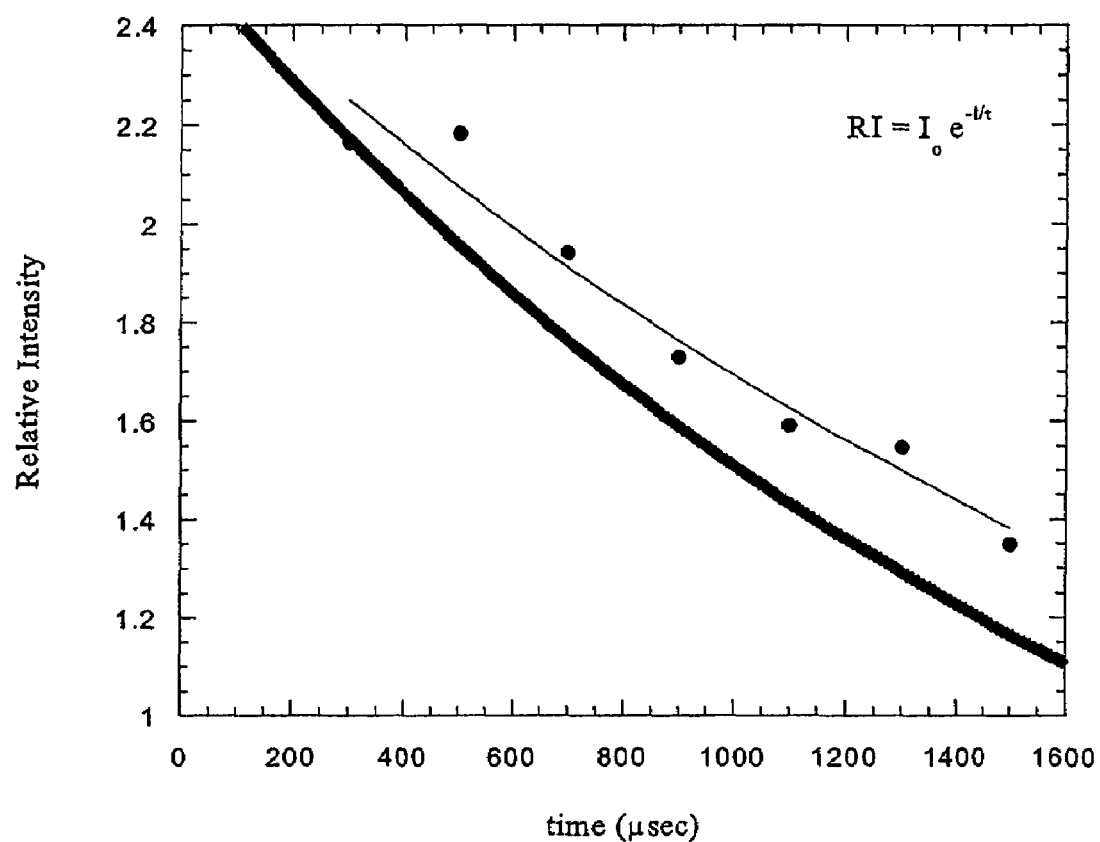
FIG. 5. Lifetime decay curves of terbium (III) in TBF and TBFBGFP at 25° C. Protein concentrations for TBF (●) and TBFEGFP (♦) were 135 nM in 10 mM Pipes; 100 mM KCl; pH 6.5 with a $Tb^{3+}$ to protein ratio of 2:1. Excitation and emission wavelength wavelengths for TBF were 285 nm and 545 nm with a cutoff filter of 455 nm and for TBFEGFP they were 295 nm and 545 nm. Measurements for TBF were taken in the middle of each 200 μsec window for a total of 8 windows. Measurements for TBFEGFP were taken with a 0.2 msec delay time and a 0.01 msec gate time FIG. 6. The excitation spectra of TBF, EGFP and TBFEGFP at 25° C. Protein concentrations were 500 nM in 10 mM Pipes; 100 mM KCl; pH 6.5 with a $Tb^{3+}$ to protein ratio of 2:1 for those spectra with $Tb^{3+}$. Symbols are TBF without $Tb^{3+}$ (○) and with $Tb^{3+}$ (●), EGFP without $Tb^{3+}$ (□) and with $Tb^{3+}$ (■), and TBFEGFP without $Tb^{3+}$ (◇) and with $Tb^{3+}$ (◆). Emission wavelengths were 350 nm (A), 490 nm (B), 510 nm (C) and 545 nm (D).

FIG. 5 shows the lifetime decay curves of TBF and TBFEGFP. The lifetime, τ, of $Tb^{3+}$ in TBF and TBFEGFP was determined to be 2.73±0.03 msec and 1.92±0.08 msec, respectively. The discrepancies between the two lifetimes is due to the energy transfer from $Tb^{3+}$ in the TBF domain in TBFEGFP to the chromophore in the EGFP domain.

Excitation Spectra

Figure 6:
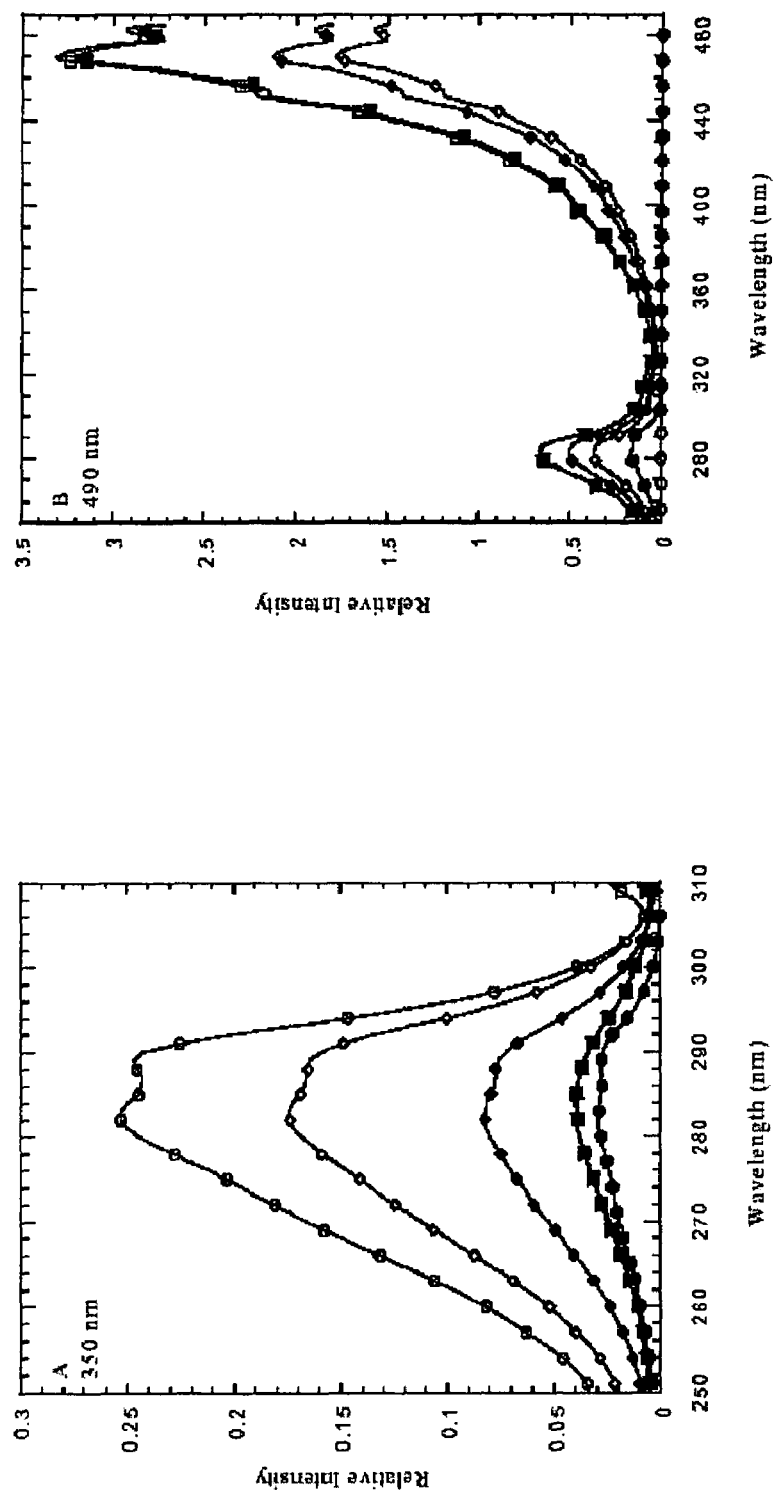

The excitation spectra of TBF, EGFP and TBFEGFP are shown in FIG. 6 with emission wavelengths of 350 nm for Trp (A), 490 nm (B) and 545 nm (D) for $Tb^{3+}$ and 510 nm for EGFP's chromophore (C).

FIG. 6A shows the excitation spectra of TBF, EGFP and TBFEGFP with and without $Tb^{3+}$ at the emission wavelength of 350 nm. From the spectra, the addition of $Tb^{3+}$ decreases the excitation of Trp for both TBF and TBFEGFP as energy is transferred to $Tb^{3+}$ and no change for EGFP. The excitation decrease in TBF is greater then the excitation decrease in TBFEGFP due to the complex energy transfer occurring in TBFEGFP. No change in the Trp excitation of EGFP is expected as $Tb^{3+}$ does not bind and it's Trp's excitation is fairly low even though it has only one Trp. However, there is an energy transfer from its Trp to the chromophore. This effect is also shown with TBFEGFP with its decreased excitation without $Tb^{3+}$ as compared to TBF without $Tb^{3+}$. It may also explain the greater increase in TBFEGFP's excitation with $Tb^{3+}$ as compared to TBF with $Tb^{3+}$.

FIG. 6B shows the excitation spectra of TBF, EGFP and TBFEGFP at the emission wavelength of 490 nm. This emission wavelength overlaps with the excitation peak of EGFP at 488 nm. There is no change in the spectra of EGFP with or without $Tb^{3+}$. However, EGFP now exhibits the greatest excitation in the Trp area as compared to FIG. 6A where EGFP's excitation is relatively small. This further adds to the idea there is energy transfer occurring between EGFP's Trp and its chromophore. The spectra of TBF and TBFEGFP both show an increase in excitation with the addition of $Tb^{3+}$ as energy is now being transferred from $Tb^{3+}$ to Trp. The discrepancies between TBF's and TBFEGFP's excitations with and without $Tb^{3+}$ are further proof of the complex energy transfer system within TBFEGFP.

FIG. 6C is the excitation spectra of the proteins at an emission wavelength of 510 nm the emission wavelength of the chromophore of EGFP. For each protein, there is no difference with or without $Tb^{3+}$. TBF exhibits no peaks as there cannot be any energy transfer due to the lack of the chromophore. Both the TBFEGFP and EGFP proteins show peaks in the Trp and chromophore areas. This is not surprising as each contains the chromophore and energy is being transferred back to the Trp. Here the energy transfer between Trp and the chromophore is witnessed. Any energy transfer between $Tb^{3+}$ and the chromophore cannot be seen here.

FIG. 6D, the spectra of the proteins are presented at the second emission wavelength of $Tb^{3+}$ at 545 nm. The small peaks at 272.5 nm (half of 545 nm) are due to second order diffraction. In this figure, there is no change in the spectra of EGFP with or without $Tb^{3+}$ in the Trp and chromophore areas due to the lack of a $Tb^{3+}$ binding site. With TBFEGFP, there is no change in the chromophore area. This indicates that it is the 490 nm peak of $Tb^{3+}$ which donates it's energy to the chromophore and not the 545 nm peak. The change in the Trp area of TBF and TBFEGFP with or without $Tb^{3+}$ is again due to the energy transfer occurring between $Tb^{3+}$ and Trp.

Emission Spectra

The steady state emission spectra of TBF, EGFP and TBFEGFP are shown in FIG. 7. FIG. 7A is the emission spectra of the proteins when excited at the excitation wavelength of Trp at 285 nm. The Trp fluorescence of all three proteins almost mimics the excitation spectra of the proteins when the emission is set at 350 nm (FIG. 6A). With TBF, the energy transfer from Trp to $Tb^{3+}$ is clearly seen, with the decrease in Trp fluorescence upon addition $Tb^{3+}$. TBFEGFP shows the same, but the difference is not so great between bound and unbound $Tb^{3+}$ and there is no change with EGFP.

The wavelength area above 480 nm is where a difference is seen. With TBF, the two characteristic peaks of $Tb^{3+}$ at 490 nm and 545 nm become visible as $Tb^{3+}$ is added. The Trp emission decreased and the $Tb^{3+}$ peaks appeared. With TBFEGFP, the two peaks of $Tb^{3+}$ are not present and only the 545 nm peak can be seen. This is due to the 490 nm peak being buried by the chromophore's peak at 510 nm. This was also observed with the titration of TBFEGFP with $TbCl_3$ (FIG. 4). With EGFP, the peak of the chromophore at 510 nm is seen. Although, it's excitation wavelength is 488 nm there is energy transfer with EGFP's Trp to the chromophore.

FIG. 7B shows the emission spectra of the proteins when excited by the chromophore of EGFP. All three show no change in emission upon addition of $Tb^{3+}$. TBF shows no peaks at all due to the lack of the chromophore, TBFEGFP shows no change as there is no energy transfer between the chromophore and the 545 nm peak of $Tb^{3+}$ and therefore exhibits the same emission spectrum as EGFP.

Due to the complex energy transfer system occurring within TBFEGFP, it is difficult to isolate the energy transfer system of $Tb^{3+}$ to the chromophore of EGFP with steady state fluorescence. Time-gated fluorescence allows one to eliminate any interference from Trp fluorescence and isolating the fluorescence due to $Tb^{3+}$. FIG. 8 shows the time-gated emission spectra of TBFEGFP with and without $Tb^{3+}$. In the absence of $Tb^{3+}$, there is no signal, but in the presence of $Tb^{3+}$ the energy transfer of $Tb^{3+}$ the chromophore of the EGFP domain is clearly seen. The two characteristic peaks of $Tb^{3+}$ are present, as well as the 510 nm peak of the chromophore.

The native and denatured states of TBF, EGFP and TBFEGFP, as monitored by Trp fluorescence, are shown in FIG. 9. The native and denatured states of TBF show emission maxima of 325 nm and 350 nm, respectively. The blue shift in fluorescence from denatured to native indicates the Trp is in a more hydrophobic environment. Although TBF is thermally stable, there is a conformational change upon addition of a high concentration of urea and $Tb^{3+}$ cannot bind. This is noted by the high fluorescence at 350 nm. In the native state, one notes the $Tb^{3+}$ is bound and has quenched the Trp fluorescence.

TBFEGFP also shows a blue shift in fluorescence from denatured to native (347 nm to 332 m), but the difference is not as great and the decrease in fluorescence is only 12%. This is due to the very stable EGFP domain. EGFP exhibits no difference between native and denatured states with emission maxima of 322 nm. EGFP has been found to be a very stable β-can protein with its chromophore deeply buried and under the protection of its β-can. EGFP has been found to be resistant to unfolding by heat ($T_m$=70° C.), alkaline pH, detergents, chaotropic salts, many organic solvents and most proteases {Bolman & Ward 1981 73/id}{Ward 1981 74/id}{Robart & Ward 1990 75/id}. The Trp of EGFP is also buried within the hydrophobic core and situated close to the chromophore. The fluorescence is blue shifted down to 322 nm. The low fluorescence is due to the energy transfer of the Trp to the chromophore as seen with the other results. So, the difference in emission fluorescence of the native and denatured states of TBFEGFP is due to the TBF domain as the EGFP. The slight blue shift in fluorescence from 347 nm to 332 nm is due to the binding of $Tb^{3+}$, and the low fluorescence is due to the complex energy transfer system within TBFEGFP.

Example 2 pTTE Construct

The pTTE construct was designed to insert the protein sequence recognized by the TEV protease between the TBF and EGFP proteins. This was accomplished by designing a primer containing the code for the TEV recognition sequence and glycines flanked on either side to ensure accessibility of the enzyme to cleave (FIG. 11). As with the pTBFEGFP construct, an amino aid linker, threonine was needed to ensure transcription remained in frame through to EGFP. The coding strand primer was the same used for designing the pTBFEGFP construct as this plasmid was used as the template. The anticoding strand was designed as follows, 5'-CGCGCCATGGTaccgccaccgccACCCTGAAAATACAA ATTCTC gccaccgccaccGGATTCAGCTACC ATTTCITG-GAACTCATCAGCTCCAATCTTACC-3' (Nco I site is in bold, codes for glycine are in lower case and the code for the TEV recognition sequence is bold and underlined) (SEQ ID NO. 11).

Amplification of the gene, restriction digest of the gene and the vector, ligation and transformation were carried out by the same method used in constructing pTBFEGFP.

Verification of ligation and transformation were carried out as previous and the new construct was named pTTE.

Purification of TTE

Purification of TIE was carried out as per the method outlined for the purification of TBF and TBFEGFP. The exception being after the final dialysis against $ddH_2O$. Instead of lyophilizing, the solution was concentrated down using an Amicon Ultrafiltration Cell (Amicon Inc.) with a NMWL 10,000 membrane. Protein purity was judged by denaturing gel electrophoresis and mass spectrometry.

TTE Cleavage with TEV Protease

To cleave the protein and yield the products TBF and EGFP, the TEV protease was used. TEV is a site-specific protease recognizing the protein sequence ENLYFQG with cleavage occuring between Q and G {Doughtery, Carrington, et al. 1988 61/id} {Carrington & Doughtery 1988 62/id} {Doughtery & Parks 1989 63/id}.

The cleavage of TTE was performed by treating 1 mg of the protein with the TEV protease (Gibco-Life Technologies) and beta-mercaptoethanol (β-ME) and incubating at 4° C. overnight to ensure complete digestion. β-ME was added as TEV protease is a cysteine protease. The reaction mixture was poured into dialysis tubing (3,500 MWCO) and dialyzed overnight against 10 mM Pipes, 100 mM KCl, pH 6.5 to remove the β-ME. The reaction mixture was then loaded onto a nickel column equilibrated with 5 mM Imidazole, pH 7.5 to remove the TEV protease. Increasing amounts of Imidazole was used for eluting the cleaved products. The 1 ml elution fractions were collected and the presence of the cleaved protein products were determined by denaturing gel electrophoresis.

Steady State Emission Spectra

Emission spectra were recorded on a PTI C-61 fluorimeter equipped with a temperature control and stirring unit using a quartz cuvette of 1 cm pathlength. Bandwidths were set to 4 nm. Protein concentrations were 227 nM with a $Tb^{3+}$ to protein ratio of 2:1 for those spectra with $Tb^{3+}$. Excitation wavelengths were set at 295 nm for Trp to monitor Trp fluorescence and 488 nm to monitor the fluorescence of the EGFP chromophore. The observed fluorescence was corrected for the contributions of the buffer and expressed as relative intensity with arbitrary units.

As cleavage of TTE and techniques used in separating the products, might not yield equimolar amounts of TBF and EGFP, concentrations of the TTE and cleaved TTE were determined using the extinction coefficient of EGFP.

Time-Gated Emission Spectra

Time-gated emission spectra were performed on an Eclipse fluorimeter equipped with a temperature control and stirring unit using a quartz cuvette of 1 cm pathlength. Bandwidths for both excitation and emission were set at 10 nm. Protein concentrations were 227 nM in 10 mM Pipes, 100 mM with a $Tb^{3+}$ to protein ratio of 2:1 for those spectra with $Tb^{3+}$. The excitation wavelength was 295 nm. The time gate window was set to 0.01 msec with a delay time of 0.20 msec. The observed fluorescence was corrected for the contributions from the buffer and expressed as relative intensity with arbitrary units.

Results

To further explore the potential of this new energy transfer system for monitoring bimolecular interactions, TTE was created TBFEGFP was modified to include the TEV protease recognition site sequence, ENLYFQG, between its two domains, TBF and EGFP, with cleavage occurring between Q and G {Doughtery, Carrington, et al. 1988 61/id} {Carrington & Doughtery 1988 62/id} {Doughtery & Parks 1989 63/id}. Glycines were flanked on either side of the recognition site to ensure accessibility of the protease to cleave. Exposing TTE to the protease, the two domains would separate eliminating the energy transfer from $Tb^{3+}$ to the EGFP chromophore.

Steady State Emission Spectra

The steady state emission spectra of the cleaved and uncleaved TIE are shown in FIG. 12. The intact TTE mimics the emission spectra of TBFEGFP. With excitation at 295 nm and in the absence of $Tb^{3+}$, there is a high Trp fluorescence at 350 nm and the 510 nm peak from the EGFP chromophore with no sign of any $Tb^{3+}$ peaks. Trp fluorescence decreases upon the addition of $Tb^{3+}$ and the 545 nm peak of $Tb^{3+}$ and the EGFP chromophore peak at 510 nm overshadow the other peak of $Tb^{3+}$ at 490 nm. With excitation at 488 nm, the spectra is the same as TBFEGFP (FIG. 7B).

The cleaved TIE has an additional peak at 380 nm. However, the spectra give a mix of TBF and EGFP. Excitation at 295 nm gives a high Trp fluorescence at 350 nm and a 510 nm peak. Upon the addition of $Tb^{3+}$, the Trp fluorescence decreases and the appearance of the 545 nm peak of $Tb^{3+}$ appears. The 490 nm peak is not present in cleaved TTE spectrum with $Tb^{3+}$ due to the two separate proteins, TBF and EGFP, existing in the same solution, so the 510 nm peak form the chromophore still overshadows the 490 nm peak of $Tb^{3+}$.

Steady state fluorescence cannot eliminate the fluorescence of one of the entities in the solution and yield spectra for both TBF and EGFP. However, it does show that both TBF and EGFP both exist in the solution.

Time-Gated Emission Spectra

With time-gated fluorescence, the problems associated with steady state fluorescence are eliminated. FIG. 13 is the time-gated emission spectra of the cleaved and uncleaved TTE. As with the time-gated emission spectra of TBFEGFP, the intact TTE has no fluorescent signal in the absence of $Tb^{3+}$, but upon addition of $Tb^{3+}$, the energy transfer from $Tb^{3+}$ to the chromophore of EGFP is clearly seen (FIG. 14A). The cleaved TTE yielded spectra reminiscent of the emission spectra of TBF. In the absence of $Tb^{3+}$, there is no fluorescent signal, but with $Tb^{3+}$, there appears the two characteristic peaks of $Tb^{3+}$ at 490 nm and 545 nm. The absence of the chromophore peak at 510 rum indicates that the energy transfer system from $Tb^{3+}$ to the chromophore is diminished.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the domains, cell lines, vectors, methodologies etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth

TABLE 1

The molecular weights of TBF, EGFP and TBFEGFP in Daltons.

| Protein | Calculated[a] | Determined[b] |
|---------|---------------|---------------|
| TBF     | 12,304.9      | 12,453.59 ± 0.43 |
| EGFP    | 26,792.87     | 26,140.56 ± 1.16 |
| TBFEGFP | 39,330.07     | 38,678.54 ± 0.97 |

[a]The molecular weight as determined by the sum of the molecular weights on the non-ionized amino acids minus that of water.
[b]The molecular weight as determined by Q-STAR mass spectrometry.

TABLE 2

The extinction coefficients of TBF, EGFP and TBFEGFP.

| Protein | $\epsilon$ $(M^{-1} cm^{-1})^{a}$ |
|---------|-----------------------------------|
| TBF     | 12,780 |
| EGFP    | 20,010 |
| TBFEGFP | 32,790 |

[a]The extinction coefficients as calculated using the data from the Edelhoch Method for a protein.

TABLE 3

Temperature of unfolding for TBF, CDOM33, OM, and OM mutants

| Proteins | $T_m{}^a$ | |
|---|---|---|
| | $-Tb^{3+}$ | $+Tb^{3+}$ |
| α-PV | 45.8 ± 0.5 | n/a |
| OM | 53.6 ± 0.5 | n/a |
| Y57W | 55.9 ± 0.5 | 81.7 ± 0.4 |
| Y65W | 52.8 ± 0.4 | 61.6 ± 0.4 |
| F102W | 50.9 ± 0.4 | 86.4 ± 0.4 |
| CDOM33 | 70.1 ± 0.5 | 87.7 ± 0.4 |
| TBF | >80 | >95 |

$^a T_m$ is defined as temperature midway through the thermal curve in °C. The $T_m$ for TBF has not been determined as a post transition region could not be obtained. Methods and other data have been previously published {Zheng, Ried, et al. 1997 54/id} {Zheng, Hogue, et al. 1998 5/id} {Henzl & Graham 1999 12/id}.

FULL CITATIONS FOR REFERENCES CITED IN THE SPECIFICATION

1. H Edelhoch: Spectroscopic determination of tryptophan and tyrosine in proteins. Biochemistry 1967, 6:1948-1954.
2. M T Henzl, R C Hapak, E R Birnbaum: Lanthanide-binding properties of rat oncomodulin. Biochim Biophys Acta 1986, 872:16-23.
3. J P MacManus, C W Hogue, B J Marsden, M Sikorska, A G Szabo: Terbium luminescence in synthetic peptide loops from calcium-binding proteins with different energy donors. J Biol Chem 1990, 265:10358-66.
4. C W Hogue, J P MacManus, D Banville, A G Szabo: Comparison of terbium (III) luminescence enhancement in mutants of EF hand calcium binding proteins. J Biol Chem 1992, 267:13340-7.
5. I D Clark, I Hill, M Sikorska-Walker, J P MacManus, A G Szabo: A novel peptide designed for sensitization of terbium (III) luminescence. FEBS Lett 1993, 333:96-8.
6. L Zheng, C W Hogue, J D Brennan: Effects of metal binding affinity on the chemical and thermal stability of site-directed mutants of rat oncomodulin. Biophys Chem 1998, 71:157-72.
7. F Gentile, E Crescenzi, C Pellegrini, M Tecce, G Palumbo: Probing the interaction of thyroglobulin with metal ions by terbium(III) luminescence spectroscopy. Mol Cell Endocrinol 1998, 141:21-7.
8. J G Stout, Q Zhou, T Wiedmer, P J Sims: Change in conformation of plasma membrane phospholipid scramblase induced by occupancy of its Ca2+ binding site. Biochemistry 1998, 37:14860-6.
9. T C Williams, D C Corson, K Oikawa, W D McCubbin, C M Kay, B D Sykes: 1H NMR spectroscopic studies of calcium-binding proteins. 3. Solution conformations of rat apo-alpha-parvalbumin and metal-bound rat alpha-parvalbumin. Biochemistry 1986, 25:1835-46.
10. C A McPhalen, A R Sielecki, B D Santarsiero, M N James: Refined crystal structure of rat parvalbumin, a mammalian alpha-lineage parvalbumin, at 2.0 A resolution. J Mol Biol 1994, 235:718-32.
11. D C Corson, T C Williams, L E Kay, B D Sykes: 1H NMR spectroscopic studies of calcium-binding proteins. 1. Stepwise proteolysis of the C-terminal alpha-helix of a helix-loop-helix metal-binding domain. Biochemistry 1986, 25:1817-26.
12. F R Ahmed, D R Rose, S V Evans, M E Pippy, R To: Refinement of recombinant oncomodulin at 1.30 A resolution. J Mol Biol 1993, 230:1216-1224.
13. M T Henzl, J S Graham Conformational stabilities of the rat alpha- and beta-parvalbumins. FEBS Lett 1999, 442:241-5.
14. M L Bhaumik, M A El-Sayed: mechanism and rate of the intramolecular energy transfer process in rare-earth chelates. J Chemical Physics 1965, 42:787-788.
15. W D Horrocks, Jr., D R Sudnick: Time-resolved europium (III) excitation spectroscopy: a luminescence probe of metal ion binding sites. Science 1979, 206:1194-6.
16. J De Jersey, M P Jeffers, R B Martin: Lanthanide probes in biological systems: characterization of luminescence excitation spectra of terbium complexes with proteins. Biophys Chem 1981, 13:233-43.
17. H G Brittain, F S Richardson, R B Martin: Terbium (III) emission as a probe of calcium(II) binding sites in proteins. J Am Chem Soc 1976, 98:8255-60.
18. C W Cody, D C Prasher, W M Westler, F G Prendergast, W W Ward: Chemical structure of the hexapeptide chromophore of the Aequorea green-fluorescent protein. Biochemistry 1993, 32:1212-8.
19. R Heim, D C Prasher, R Y Tsien: Wavelength mutations and posttranslational autoxidation of green fluorescent protein. Proc Natl Acad Sci U S A 1994, 91:12501-4.
20. D F Davis, W W Ward, M W Cutler: Posttranslational chromophore formation in recombinant GFP from E. coli requires oxygen. In: Proceedings from the 8th international symposium on bioluminescence and chemiluminescence; 1995.
21. G H Patterson, S M Knobel, W D Sharif, S R Kain, D W Piston: Use of the green fluorescent protein and its mutants in quantitative fluorescence microscopy. Biophys J 1997, 73:2782-90.
22. J R Lakowicz: Principles of fluorescence spectroscopy, 2 edn. New York: Kulwer Academic/Plenum Publishers; 1999.
23. P R Selvin, J E Hearst: Luminescence energy transfer using a terbium chelate: Improvements on fluorescence energy transfer. Proc Natl Acad Sci USA 1994, 91:10024-10028.
24. M Li, P R Selvin: Luminescent polyaminocarboxylate chelates of terbium and europium: The effect of chelate structure. J Am Chem Soc 1995, 117:8132-8138.
25. J Chen, P R Selvin: Thiol-reactive luminescent chelates of terbium and europiuml Bioconjug Chem 1999, 10:311-5.
26. N Sabbitini, M Guardigli, J-M Lehn: Luminescent lanthanide complexes as photochemical supramolecular devices. Coord. Chem. Rev. 1993, 123:201-228.
27. S H Bokman, W W Ward: Renaturation of Aequorea green-fluorescent protein. Biochem Biophys Res Commun 1981, 101:1372-80.
28. W W Ward: Properties of the Coelenterate green-fluorescent proteins. In: Bioluminescence and Chemiluminescence: basic Chemistry and Analytical applications Edited by M DeLuca, W D McElroy. pp. 235-242. New York: Academic Press, Inc.; 1981: 235-242.
29. F O Robart, W W Ward: Solvent perturbations of Aequorea green fluorescent protein. Photocher. Photobiol. 1990, 51:92s.
30. W Dougherty, J Carrington, S Cary, T Parks: Biochemical and mutational analysis of a plant virus polyprotein cleavage site. EMBO J. 1988, 7:1281-1287.
31. J C Carrington, W Dougherty: A viral cleavage site cassette: identification of amino acid sequences required for tobacco etch virus polyprotein processing. Proc Natl Acad Sci U S A 1988, 85:3391-3395.
32. W Dougherty, T D Parks, S M Cary, J F Bazan, R J Fletterick: Characterization of the catalytic residues of the tobacco etch virus 49 kDa protein. Virology 1989, 172:302-310.

We claim:

1. A luminescent protein comprising oncomodulin in which:
   (a) Gln27 of oncomodulin is replaced with Lys27;
   (b) Ser36 of oncomodulin is replaced with Lys36;
   (c) C-terminus has been extended;
   (d) one or more salt bridges and/or hydrogen bonding networks have been introduced to provide greater stability when compared to a native oncomodulin or CDOM33; and
   (e) $Tb^{3+}$ luminescence is enhanced relative to CDOM33.

2. A luminescent protein as claimed in claim 1 comprising the amino acid sequence of SEQ ID NO. 5.

3. The luminescent protein of claim 1, wherein the luminescent protein is associated or conjugated with one or more molecules and in the form of a chimeric protein.

4. The luminescent protein of claim 3 wherein the molecule is a luminescent agent acceptor or target peptide.

5. The luminescent protein of claim 4 wherein the luminescent agent acceptor is a green fluorescent protein.

6. The luminescent protein of claim 1 in combination with at least one component of a bioluminescence-generating system.

7. The luminescent protein of claim 6 wherein the bioluminescence generating system is a green fluorescent protein system.

8. The luminescent protein of claim 1, further comprising a complexed metal ion.

9. The luminescent protein of claim 8, wherein the metal ion is a lanthanide ion.

10. The luminescent protein of claim 8, wherein the metal ion is a terbium ion.

11. A luminescent protein comprising oncomodulin comprising the amino acid sequence of SEQ ID NO. 5 in which one or more salt bridges and/or hydrogen bonding networks have been introduced to provide greater stability when compared to a native oncomodulin or CDOM33.

12. The luminescent protein of claim 11, wherein the luminescent protein is associated or conjugated with one or more molecules and in the form of a chimeric protein.

13. The luminescent protein of claim 12, wherein the luminescent protein is associated or conjugated with a luminescent agent acceptor or target peptide.

14. The luminescent protein of claim 13, wherein the luminescent agent acceptor is a green fluorescent protein.

15. The luminescent protein of claim 11, in combination with at least one component of a bioluminescence-generating system.

16. The luminescent protein of claim 15, wherein the bioluminescence generating system is a green fluorescent protein system.

17. The luminescent protein of claim 11, further comprising a complexed metal ion.

18. The luminescent protein of claim 17, wherein the metal ion is a lanthanide ion.

19. The luminescent protein of claim 18, wherein the metal ion is a terbium ion.

20. A luminescent protein comprising oncomodulin in which Gln27 is replaced with Lys27, Ser36 is replaced with Lys36; and a C-terminus is extended.

21. The luminescent protein of claim 20, comprising the amino acid sequence of SEQ ID NO. 5.

22. The luminescent protein of claim 20, wherein the luminescent protein is associated or conjugated with one or more molecules and in the form of a chimeric protein.

23. The luminescent protein of claim 22, wherein the luminescent protein is associated or conjugated with a luminescent agent acceptor or target peptide.

24. The luminescent protein of claim 23, wherein the luminescent agent acceptor is a green fluorescent protein.

25. The luminescent protein of claim 20, in combination with at least one component of a bioluminescence-generating system.

26. The luminescent protein of claim 25, wherein the bioluminescence generating system is a green fluorescent protein system.

27. The luminescent protein of claim 20, further comprising a complexed metal ion.

28. The luminescent protein of claim 27, wherein the metal ion is a lanthanide ion.

29. The luminescent protein of claim 28, wherein the metal ion is a terbium ion.

* * * * *